(12) United States Patent
Zauhar et al.

(10) Patent No.: US 8,200,439 B2
(45) Date of Patent: Jun. 12, 2012

(54) COMPUTER AIDED LIGAND-BASED AND RECEPTOR-BASED DRUG DESIGN UTILIZING MOLECULAR SHAPE AND ELECTROSTATIC COMPLEMENTARITY

(76) Inventors: Randy J. Zauhar, Philadelphia, PA (US); William J. Welsh, Princeton, NJ (US)

( * ) Notice: Subject to any disclaimer, the term of this patent is extended or adjusted under 35 U.S.C. 154(b) by 0 days.

(21) Appl. No.: 12/904,968

(22) Filed: Oct. 14, 2010

(65) Prior Publication Data

US 2011/0066384 A1    Mar. 17, 2011

Related U.S. Application Data

(60) Division of application No. 11/870,279, filed on Oct. 10, 2007, now Pat. No. 8,140,311, which is a continuation-in-part of application No. 10/635,280, filed on Aug. 6, 2003, now abandoned.

(60) Provisional application No. 60/401,637, filed on Aug. 6, 2002.

(51) Int. Cl.
  G06F 19/00    (2011.01)
  G01N 33/48    (2006.01)

(52) U.S. Cl. ........................................................ 702/19

(58) Field of Classification Search .................. None
See application file for complete search history.

(56) References Cited

OTHER PUBLICATIONS

Klebe, G., "Recent developments in structure-based drug design," J Mol Med, 2000, pp. 269-281, Springer-Verlag.
Connolly, M.L., "Analytical Molecular Surface Calculation," J. Appl. Cryst., 1983, pp. 548-558, International Union of Crystallography, U.S.A.
Chen, Z., Li, Y., Chen, E., Hall, D.L., Darke, P.L., Culberson, C., Shafer, J.A. and Kuo, L.C., "Crystal Structure at 1.9-A Resolution of Human Immunodeficiency Virus (HIV) II Protease Complexed with L-735,524, an Orally Bioavailable Inhibitor of the HIV Proteases," The Journal of Biological Chemistry, 1994, pp. 26344-26348, vol. 269, No. 42, U.S.A.
Willett, P., "Chemical Similarity Searching," J. Chem. Inf. Comput. Sci., 1998, pp. 983-996, American Chemical Society.
Hahn, M., "Three-Dimensional Shape-Based Searching of Conformationally Flexible Compounds," J. Chem. Inf. Comput. Sci., 1997, pp. 80-86, American Chemical Society.
Raymond, J.W., and Willett, P., "Maximum common subgraph isomorphism algorithms for the matching of chemical structures," Journal of Computer-Aided Molecular Design, 2002, pp. 521-533, Kluwer Academic Publishers, Netherlands
Thorner, D.A., Willett, P., Wright, P.M., and Taylor, R., "Similarity searching in files of three-dimensional chemical structures: Representation and searching of molecular electrostatic potentials using field-graphs," Journal of Computer-Aided Molecular Design, 1997, pp. 163-174, ESCOM Science Publshers B.V.
Polanski, J. and Walczak, B., "The comparative molecular surface analysis (COMSA): a novel tool for molecular design," Computers and Chemistry, 2000, pp. 615-625, Elsevier Science Ltd.
Hull, R.D., Singh, S.B., Nachbar, R.B., Sheridan, R.P., Kearsley, S.K., and Fluder, E.M., "Latent Semantic Structure Indexing (LaSSI) for Defining Chemical Similarity," J. Med. Chem., 2001, pp. 1177-1184, American Chemical Society.
Van Drie, J.H., "'Shrink-Wrap' Surfaces: A New Method for Incorporating Shape Into Pharmacophoric 3D Database Searching," J. Chem. Inf. Comput. Sci., 1997, pp. 38-42, American Chemical Society.
Lawrence, M.C. and Colman, P.M., "Shape Complementarity at Protein/Protein Interfaces," J. Mol. Biol., 1993, pp. 946-950, Academic Press Limited.
Putta, S., Lemmen, C., Beroza, P., and Greene, J., "A Novel Shape-Feature Based Approach to Virtual Library Screening," J. Chem. Inf. Comput. Sci., 2002, pp. 1230-1240, American Chemical Society.
Milne, G.W.A., Feldman, A., Miller, J.A., and Daly, G.P., "The NCI Drug Information System. 3. The DIS Chemistry Module," J. Chem. Inf. Comput. Sci., 1986, pp. 168-179, American Chemical Society.
Cramer, R.D., "Topomer CoMFA: A Design Methodology for Rapid Lead Optimization," J. Med. Chem., 2003, pp. 374-388, American Chemical Society.
Gasteiger, J. and Marsili, M., "Iterative Partial Equalization of Orbital Electronegativity—A Rapid Access to Atomic Charges," Tetrahedron, 1980, pp. 3219-3228, vol. 36.
Ewing, T.J.A., Makino, S., Skillman, A.G., and Kuntz, I.D., "DOCK 4.0: Search strategies for automated molecular docking of flexible molecule databases," Journal of Computer-Aided Molecular Design, 2001, pp. 411-428, Kluwer Academic Publishers, Netherlands.
Miller, M.D., Kearsley, S.K., Underwood, D.J., and Sheridan, R.P., "FLOG: A system to select 'quasi-flexible' ligands complementary to a receptor of known three-dimensional structure," Journal of Computer-Aided Molecular Design, 1994, pp. 153-174, ESCOM Science Publishers B.V.
Jones, G., Willett, P., Glen, R.C., Leach, A.R., and Taylor, R., "Development and Validation of a Genetic Algorithm for Flexible Docking," J. Mol. Biol., 1997, pp. 727-748, Academic Press Limited.
Sitkoff, D., Sharp, K.A., and Honig, B., "Accurate Calculation of Hydration Free Energies Using Macroscopic Solvent Models," J. Phys. Chem., 1994, pp. 1978-1988, American Chemical Society.
Zauhar, R.J., "Smart: A solvent-accessible triangulated surface generator for molecular graphics and boundary element applications," Journal of Computer-Aided Molecular Design, 1995, pp. 149-159, ESCOM Science Publishers B.V.
Connolly, M.L., "Solvent-Accessible Surfaces of Proteins and Nucleic Acids," Science, 1983, pp. 709-713, vol. 221, No. 4612.
Richards, F.M., "Areas, Volumes, Packing and Protein Structure," Ann. Rev. Biophys. Bioeng., 1977, pp. 151-176, Annual Reviews Inc.
Kuntz, I.D., Blaney, J.M., Oatley, S.J., Langridge, R., and Ferrin, T.E., "A Geometric Approach to Macromolecule—Ligand Interactions," J. Mol. Bio., 1982, pp. 269-288, Academic Press Inc., London, England.
Xue, L. and Bajorath, J., "Molecular Descriptors in Chemoinformatics, Computational Combinatorial Chemistry, and Virtual Screening," Combinatorial Chemistry & High Throughput Screening, 2000, pp. 363-372, Bentham Science Publishers Ltd.

(Continued)

Primary Examiner — Michael Borin
(74) Attorney, Agent, or Firm — Lewis, Rice & Fingersh, L.C.

(57) ABSTRACT

Methods related to the generation of shape signatures representing molecular shape, and using shape signatures in both ligand-based and receptor-based molecular design. Ray-tracing is used to explore the volume interior to a ligand, or the space exterior to a receptor site. Shape signatures are then probability distributions derived from the ray-traces. Shape signatures provide condensed descriptors of shape properties readily compared to each other to test for shape similarity or complementarity.

3 Claims, 33 Drawing Sheets

OTHER PUBLICATIONS

Waszkowycz, B., "Structure-based approaches to drug design and virtual screening," Current Opinion in Drug Discovery & Development, 2002, pp. 407-413, PharmaPress Ltd.

Milne, G.W.A., "The NCI Drug Information System. 1. System Overview," J. Chem. Inf. Comput. Sci., 1986, pp. 154-159, American Chemical Society.

Meek, P.J., Liu, Z., Tian, L., Wang, C., Welsh, W.J., and Zauhar, R.J., "Shape signatures: speeding up computer aided drug discovery," Drug Discovery Today, 2006, pp. 895-904, vol. II, Issues 19-20, Elsevier Ltd.

Wang, C.Y., Ai., N., Arora, S., Erenrich, E., Nagarajan, K., Zauhar, R., Young, D., and Welsh, W.J., "Identification of Previously Unrecognized Antiestrogenic Chemicals Using a Novel Virtual Screening Approach," Chem. Res. Toxicol., 2006, pp. 1595-1601, American Chemical Society.

Zauhar, R. J., Moyna, G., Tian, L., Li, Z. and Welsh, W.J., "Shape Signatures: A New Approach to Computer-Aided Ligand- and Receptor-Based Drug Design," J. Med. Chem., 2003, pp. 5674-5690, American Chemical Society.

Nagarajan, K., Zauhar, R., and Welsh, W.J., "Enrichment of Ligands for the Serotonin Receptor Using the Shape Signatures Approach," J. Chem. Inf. Model., 2005, pp. 49-57, American Chemical Society.

Zhang, Q., Keenan, S.M., Peng, Y., Nair, A.C., Yu, S.J., Howells, R.D., and Welsh, W.J., "Discovery of Novel Triazole-Based Opioid Receptor Antagonists," J. Med. Chem., 2006, pp. 4044-4047, American Chemical Society.

Zauhar, R., Fretz, J., and Welsh, W., "Application of Shape Signatures to the Identification of Estrogenic Compounds," http://tonga.usip.edu/zauhar/Dayton_HTML/index.htm, presented at the Issues and Applications in Toxicology and Risk Assessment Meeting (EPA/USAF) on Apr. 2001 in Dayton, OH.

Zauhar, R.J., Welsh, W.J., and Moyna, G., "'Surface Signatures:' a New Approach for Fast Database Screening and Docking," http://tonga.usip.edu/zauhar/New_Orleans_HTML/index.htm, presented at the ACS National Meeting on Aug. 1999 in New Orleans, LA.

Zauhar, R., "Welcome to the Home Page for Randy J. Zauhar, PhD," http://tonga.usip.edu/zauhar/, printed on Jan. 15, 2008.

Zauhar, R., "Supplement, Shape Signatures," 1999, pp. 1-3.

Milne, G.W.A. and Feldman, A., "The NCI Drug Information System. 2. DIS Pre-Registry," J. Chem. Inf. Comput. Sci., 1986, pp. 159-168, American Chemical Society.

Milne, G.W.A., "The NCI Drug Information System. 4. Inventory and Shipping Modules," J. Chem. Inf. Comput. Sci., 1986, pp. 179-185, American Chemical Society.

Miller, J.A., "The NCI Drug Information System. 5. DIS Biology Module," J. Chem. Inf. Comput. Sci., 1986, pp. 186-193, American Chemical Society.

Zehnacker, M.T., Brennan, R.H., and Milne, G.W.A., "The NCI Drug Information System. 6. System Maintenance," J. Chem. Inf. Comput. Sci., 1986, pp. 193-197, American Chemical Society.

Sundling, C.M. and Breneman, C.M., "Advances in Electronic Property-Encoded Molecular Shape Descriptors," http://tonga.usip.edu/zauhar/Matt_Sundling_ACS/index.htm, presented in 2001 in San Diego, CA.

Zauhar, R., "Shape Signatures, a Promising New Tool for Computer-Aided Drug Design," http://tonga.usip.edu/zauhar/Villanova_Nov2002/Presentation.htm, presented at Villanova University on Nov. 14, 2002.

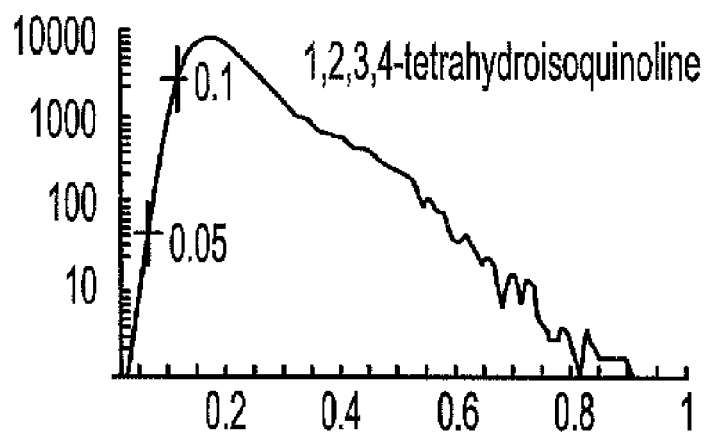
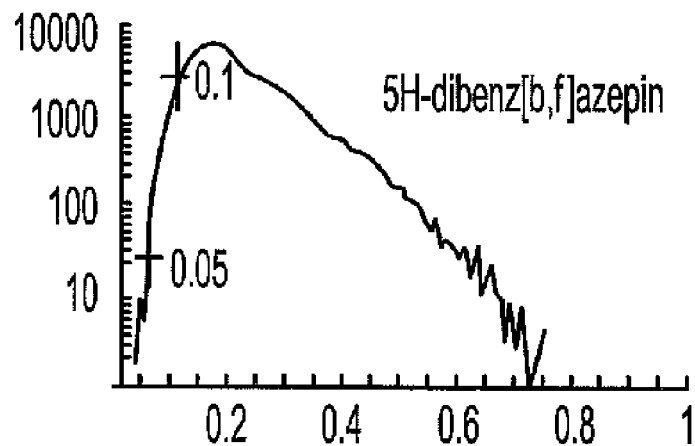
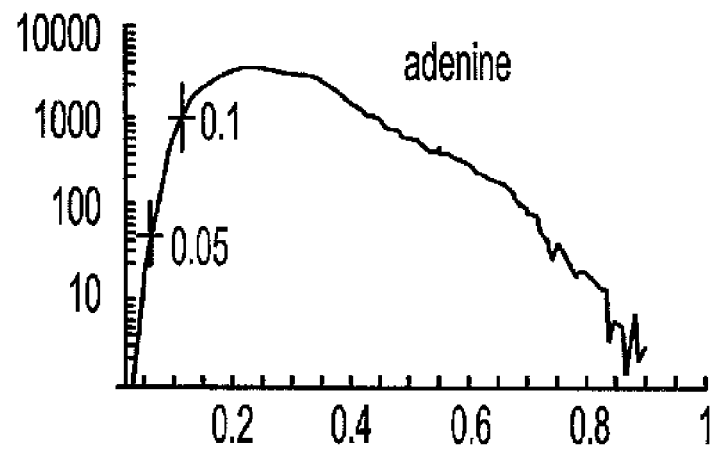
FIG. 10A

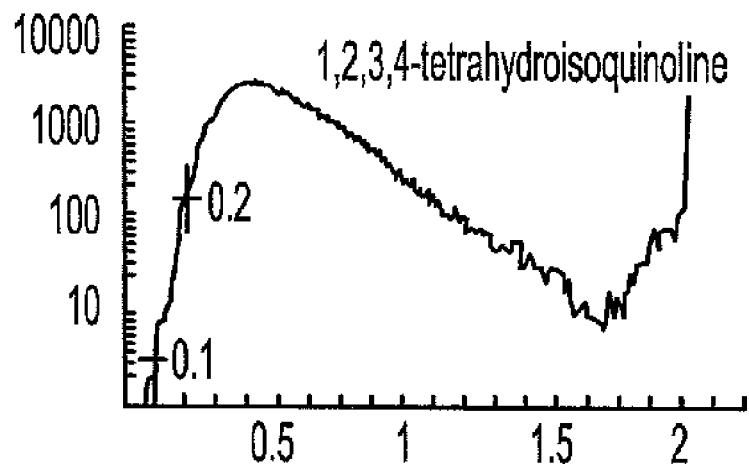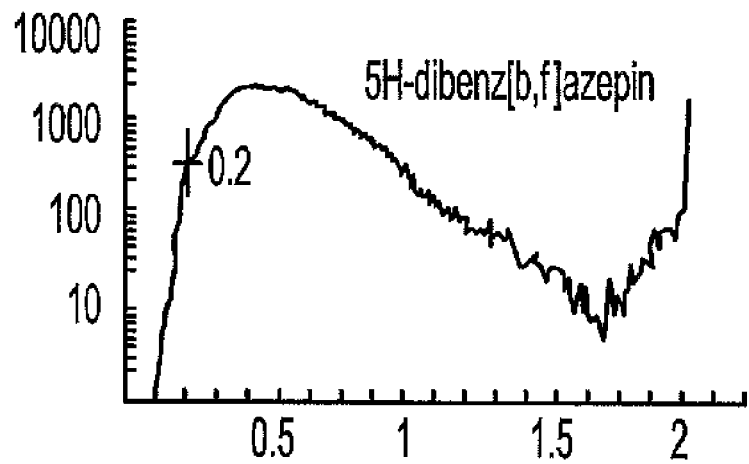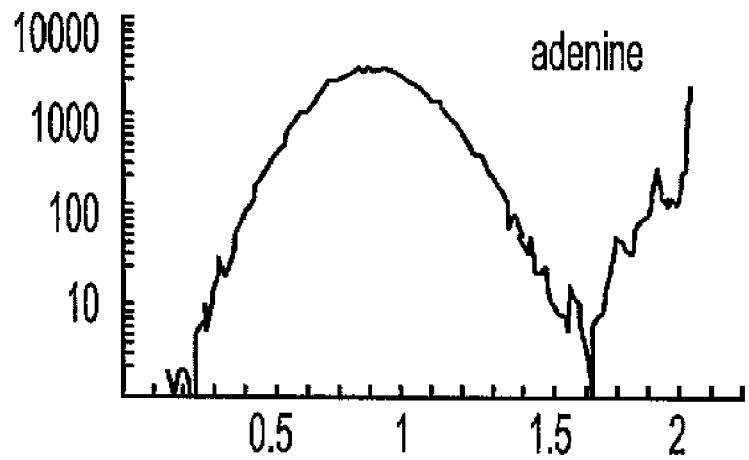
FIG. 10B

| | | | | |
|---|---|---|---|---|
| 1,2,3,4-tetrahydroisoquinoline | 1,2,3,4-tetrahydroquinoline<br>isochroman<br>1,2,3,4-tetrahydronaphthalene<br>chroman<br>indoline | 0.0370<br>0.0386<br>0.0490<br>0.0574<br>0.0767 | 1,2,3,4-tetrahydroquinoline<br>isochroman<br>chroman<br>1,2,3,4-tetrahydronaphthalene<br>indan | 0.0173<br>0.0316<br>0.0399<br>0.0475<br>0.0525 |
| 5H-dibenz[b,f]azepin | dibenzocycloheptatriene<br>dihydrophenanthrene<br>thioxanthene<br>dibenz[b,f]thiepin<br>5H-dibenzo[b,f]-1,4-diazepine | 0.0351<br>0.0482<br>0.0578<br>0.0695<br>0.0800 | dibenzocycloheptatriene<br>dihydrophenanthrene<br>thioxanthene<br>5H-dibenzo[b,f]-1,4diazepine<br>dibenz[b,f]thiepin | 0.0332<br>0.0384<br>0.0466<br>0.0487<br>0.0578 |
| 1,4,6-gonatriene-3,17-dione | 4,6-gonadiene-3,17-dione<br>1,4-gonadien-3-one<br>4-gonen-3-one<br>1,3,5(10)-gonatriene<br>5(10)-gonen-3-one | 0.0502<br>0.0743<br>0.0984<br>0.0986<br>0.1004 | 4,6-gonadiene-3,17-dione<br>1,4-gonadien-3-one<br>4-gonen-3-one<br>1,3,5(10)-gonatriene<br>5(10)-gonen-3-one | 0.0400<br>0.0660<br>0.0838<br>0.0862<br>0.0984 |
| α-D-glucopyranose | β-D-mannopyranose<br>β-D-galactopyranose<br>α-D-mannopyranose<br>α-D-galactopyranose<br>β-D-glucopyranose | 0.0417<br>0.0420<br>0.0559<br>0.0744<br>0.0748 | α-D-mannopyranose<br>β-D-mannopyranose<br>β-D-galactopyranose<br>α-D-galactopyranose<br>β-D-glucopyranose | 0.0376<br>0.0379<br>0.0391<br>0.0560<br>0.0766 |
| Lysine | Arginine<br>Methionine<br>Palmitoleate(C16)<br>glycerol(-H)<br>Oleate(C18) | 0.0862<br>0.1024<br>0.1163<br>0.1179<br>0.1202 | Methionine<br>Arginine<br>Laurate(C12)<br>Palmitoleate(C16)<br>Myristate(C14) | 0.0527<br>0.0821<br>0.0959<br>0.1004<br>0.1006 |
| adenine | guanine<br>7H-purine<br>cytosine<br>uracil<br>benzopyrimidine | 0.0626<br>0.0712<br>0.0840<br>0.0854<br>0.0860 | guanine<br>7H-purine<br>benzimidazole<br>1H-indazole<br>benzoxazole | 0.0388<br>0.0701<br>0.0743<br>0.0747<br>0.0775 |

FIG. 14A

FIG. 14B $L_1$ Metric

| QUERY | Culling | | No Culling | |
|---|---|---|---|---|
| | Hit | Score | Hit | Score |
| 1,2,3,4-tetrahydroisoquinoline | 1,2,3,4-tetrahydroquinoline<br>1,2,3,4-tetrahydronaphthalene<br>indoline<br>acenaphthene<br>indan | 0.0847<br>0.1496<br>0.1732<br>0.1908<br>0.2161 | 1,2,3,4-tetrahydroquinoline<br>1,2,3,4-tetrahydronaphthalene<br>indoline<br>indan<br>ace naphthene | 0.0762<br>0.1307<br>0.1320<br>0.1554<br>0.1804 |
| 5H-dibenz[b,f]azepin | dibenzocycloheptatriene<br>acridan<br>5H-dibenzo[b,f]-1,4-diazepine<br>1,2,3,4-tetrahydroisoquinoline<br>1,2,3,4-tetrahydroquinoline | 0.1116<br>0.2089<br>0.2109<br>0.2268<br>0.2292 | dibenzocycloheptatriene<br>acridan<br>5H-dibenzo[b,f]-1,4-diazepine<br>phenanthridine<br>dihydrophenanthrene | 0.1031<br>0.1538<br>0.1672<br>0.1762<br>0.1802 |
| 1,4,6-gonatriene-3,17-doine | 4,6-gonadiene-3,17-dione<br>5a-gonane-3,17-dione<br>1,4-gonadien-3-one<br>5a-gonan-3-one<br>5a-gonan-17-one | 0.0888<br>0.1383<br>0.2028<br>0.2031<br>0.2211 | 4,6-gonadiene-3,17-dione<br>5a-gonane-3,17-dione<br>1,4-gonadien-3-one<br>4-gonen-3-one<br>5a-gonan-3-one | 0.0852<br>0.1383<br>0.2097<br>0.2122<br>0.2221 |
| 2-deoxy-β-D-ribofuranose | β-D-ribofuranose<br>β-D-glucopyranose<br>α-D-fructofuranose<br>α-D-galactopyranose<br>α-D-mannopyranose | 0.2292<br>0.2368<br>0.2480<br>0.2616<br>0.2696 | β-D-glucopyranose<br>α-D-fructofuranose<br>α-D-mannopyranose<br>β-D-ribofuranose<br>α-D-glucopyranose | 0.2223<br>0.2317<br>0.2437<br>0.2445<br>0.2575 |
| Lysine | Arginine<br>ethanolamine<br>choline<br>D-Thrcose<br>D-Xylose | 0.6615<br>0.7882<br>1.2682<br>1.5332<br>1.5667 | Arginine<br>ethanolamine<br>choline<br>D-Thrcose<br>D-Xylose | 0.6617<br>0.7621<br>1.2442<br>1.4601<br>1.4912 |
| adenine | pteridine<br>benzothiazole<br>guanine<br>7H-purine<br>indene | 0.4025<br>0.4321<br>0.4394<br>0.4427<br>0.4614 | benzothiazole<br>pteridine<br>thiazole<br>7H-purine<br>guanine | 0.3493<br>0.3816<br>0.3981<br>0.4254<br>0.4265 |

FIG. 15

| QUERY | $L_1$ Metric | | $R_1$ Metric | |
|---|---|---|---|---|
| | Hit | Score | Hit | Score |
| 1,2,3,4-tetrahydroisoquinoline | 91-21-4<br>10500-57-9<br>529-35-1<br>578-54-1<br>24206-39-1 | 0.0291<br>0.0336<br>0.0348<br>0.0380<br>0.0397 | 91-21-4<br>10500-57-9<br>578-54-1<br>493-05-0<br>529-35-1 | 0.1153<br>0.1409<br>0.1428<br>0.1534<br>0.1743 |
| 5H-dibenz[b,f]azepin | 833-48-7<br>1211-06-9<br>10354-00-4<br>82-53-1<br>6279-16-9 | 0.0324<br>0.0360<br>0.0415<br>0.0441<br>0.0488 | 833-48-7<br>1211-06-9<br>10354-00-4<br>42263-75-2<br>51087-02-6 | 0.1404<br>0.1673<br>0.1789<br>0.2142<br>0.2300 |
| 1,4,6-gonatriene-3,17-dione | 24640-00-4<br>10448-96-1<br>438-67-5<br>5976-74-9<br>6126-58-5 | 0.0450<br>0.0556<br>0.0570<br>0.0576<br>0.0584 | 6126-58-5<br>24640-00-4<br>6968-06-5<br>20919-82-8<br>3601-97-6 | 0.2289<br>0.2561<br>0.2672<br>0.2908<br>0.2963 |
| $\alpha$-D-glucopyranose | 488-66-4<br>23559-36-6<br>74561-03-8<br>16505-91-2<br>39392-65-9 | 0.0546<br>0.0548<br>0.0553<br>0.0607<br>0.0655 | 74561-03-8<br>488-66-4<br>488-64-2<br>6623-68-3<br>2037-48-1 | 0.2223<br>0.2548<br>0.2548<br>0.2548<br>0.2549 |
| Lysine | 5329-79-3<br>110-97-4<br>5343-35-1<br>37149-01-2<br>7356-00-5 | 0.0478<br>0.0486<br>0.0552<br>0.0555<br>0.0563 | 37149-01-2<br>6963-39-9<br>110-97-4<br>6281-43-2<br>104-50-7 | 0.1874<br>0.1882<br>0.2107<br>0.2201<br>0.2224 |
| adenine | 10325-61-8<br>54346-27-9<br>73-24-5<br>1123-54-2<br>2227-98-7 | 0.0271<br>0.0304<br>0.0310<br>0.0343<br>0.0353 | 10325-61-8<br>54346-27-9<br>5426-35-7<br>73-24-5<br>19165-47-0 | 0.0944<br>0.0988<br>0.1178<br>0.1178<br>0.1178 |

FIG. 16A

| QUERY | $L_1$ Metric | | $R_1$ Metric | |
|---|---|---|---|---|
| | Hit | Score | Hit | Score |
| 1,2,3,4-tetrahydroisoquinoline | 91-21-4<br>635-46-1<br>1484-19-1<br>1780-19-4<br>5344-99-0 | 0.0701<br>0.0816<br>0.0940<br>0.0983<br>0.1011 | 91-21-4<br>635-46-1<br>1484-19-1<br>5344-99-0<br>1780-19-4 | 0.5232<br>0.6553<br>0.6977<br>0.7295<br>0.8070 |
| 5H-dibenz[b,f]azepin | 30646-39-0<br>16886-10-5<br>32446-13-2<br>3377-71-7<br>833-48-7 | 0.0947<br>0.1079<br>0.1089<br>0.1126<br>0.1167 | 30646-39-0<br>3377-71-7<br>16886-10-5<br>32446-13-2<br>833-48-7 | 0.8078<br>0.9075<br>0.9104<br>0.9166<br>0.9411 |
| 1,4,6-gonatriene-3,17-dione | 56763-86-1<br>734-32-7<br>93998-31-3<br>20056-05-7<br>74924-17-7 | 0.1524<br>0.1645<br>0.1682<br>0.1693<br>0.1702 | 20056-05-7<br>56763-86-1<br>74924-17-7<br>734-32-7<br>71837-43-9 | 1.3418<br>1.3451<br>1.4169<br>1.4949<br>1.5131 |
| α-D-glucopyranose | 52019-14-4<br>49871-87-6<br>58691-27-3<br>7404-25-3<br>14215-77-1 | 0.1815<br>0.1833<br>0.1912<br>0.2015<br>0.2018 | 52019-14-4<br>58691-27-3<br>49871-87-6<br>2280-44-6<br>14215-77-1 | 1.4065<br>1.4270<br>1.4514<br>1.5418<br>1.5520 |
| Lysine | 42021-74-9<br>58048-33-2<br>58048-35-4<br>37082-52-3<br>78582-26-0 | 0.5473<br>0.5549<br>0.5684<br>0.5719<br>0.5721 | 85385-47-3<br>58048-33-2<br>42021-74-9<br>78582-26-0<br>62194-88-1 | 4.1381<br>4.2359<br>4.2441<br>4.3301<br>4.3458 |
| adenine | 73-24-5<br>28128-33-8<br>7390-62-7<br>2846-89-1<br>3647-48-1 | 0.0683<br>0.1537<br>0.1581<br>0.1744<br>0.1820 | 73-24-5<br>28128-33-8<br>7390-62-7<br>2846-89-1<br>1904-98-9 | 0.5048<br>1.0824<br>1.2106<br>1.2491<br>1.2947 |

FIG. 17A

| RANK | ENERGY(kcal/mol) | STRUCTURE |
|---|---|---|
| #1 | -117.3 | 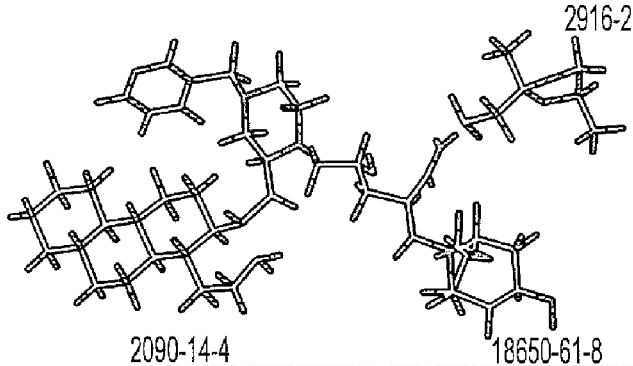 2916-28-1 / 2090-14-4 / 18650-61-8 |
| #2 | -117.0 | 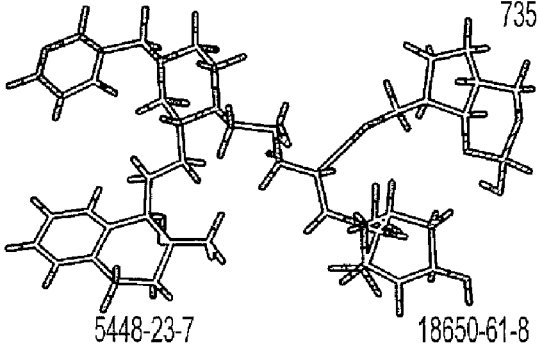 73581-87-0 / 5448-23-7 / 18650-61-8 |
| #3 | -115.2 | 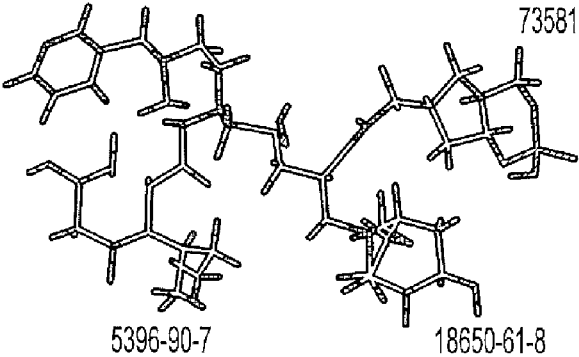 73581-87-0 / 5396-90-7 / 18650-61-8 |
| #4 | -97.2 | 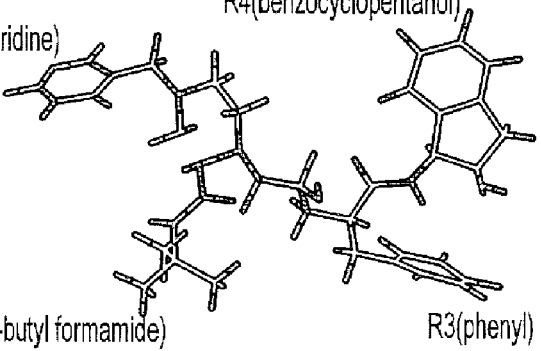 R1(pyridine), R4(benzocyclopentanol), R2(t-butyl formamide), R3(phenyl) |
FIG. 19

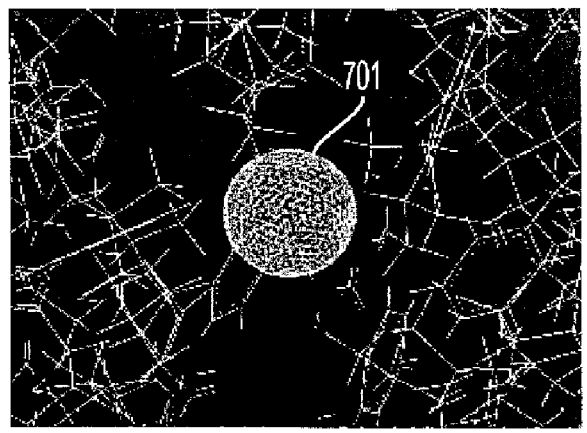
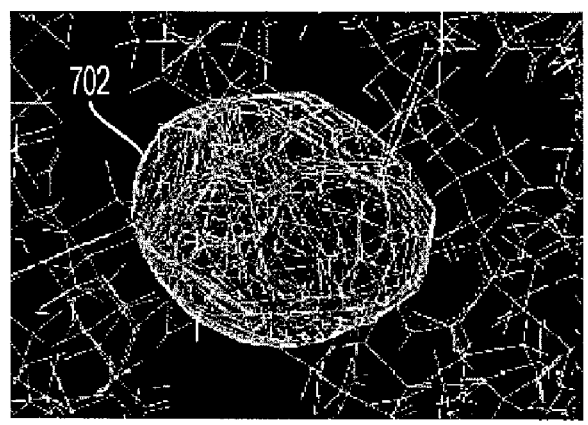
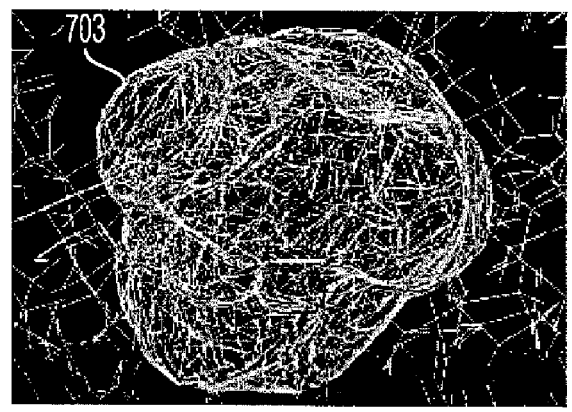
FIG. 20

COMPUTER AIDED LIGAND-BASED AND RECEPTOR-BASED DRUG DESIGN UTILIZING MOLECULAR SHAPE AND ELECTROSTATIC COMPLEMENTARITY

CROSS REFERENCE TO RELATED APPLICATIONS

This application is a Divisional of U.S. Utility application Ser. No. 11/870,279 filed Oct. 10, 2007 and now U.S. Pat. No. 8,140,311, which is, in turn, a Continuation-in-Part (CIP) of U.S. Utility application Ser. No. 10/635,280, filed Aug. 6, 2003, now abandoned, which in turn claims benefit of U.S. Provisional Patent Application Ser. No. 60/401,637, filed Aug. 6, 2002. The entire disclosure of all the above documents is herein incorporated by reference.

BACKGROUND

1. Field of the Invention

This disclosure relates to the field of computer-aided molecule design, and in particular, to utilizing shape similarity and electrostatic complementarity of molecules, as evidenced using ray-tracing techniques, to quickly compare compounds with each other and ligands with receptors.

2. Description of the Related Art

It is generally presumed in biology that a biologically-active compound having a particular effect on certain biological processes is biologically active because of its ability to interact with a complementary receptor. This principle guides drug design, chemical warfare, nutrition toxicology, and the understanding of biochemical processes of disease and normal body functioning. Biological activity is further presumed to be due at least in part to the molecule's shape. Simply put, a square peg will fit in a square hole while a round peg will fit in a round hole; understanding and directing biological activity is simply locating the correctly shaped peg (i.e., ligand) for the correctly shaped hole (i.e., receptor). Because of this principle of complementarity between a molecule and a receptor site, it is generally believed that molecules which have a shape known to be complementary to the receptor site, or a shape similar to a known biologically-active molecule, will have a higher probability of being biologically active with that receptor.

Biological activity between receptors and ligands is also believed to depend in part on electrostatic complementarity: that is, whether the hydrogen bond donors of the ligand are positioned near hydrogen bond receivers of the receptor, and vice versa. In such an arrangement, electrical charges of opposite sign are brought into close proximity, facilitating biological activity. It is not believed to be necessary for the receptor and ligand to have identical electrostatic potential, but rather, simply opposite signs at interacting positions. Similarly, molecules that are believed to have similar biological activity are believed to require only the same signed-charge (i.e., positive or negative) at corresponding positions. A molecule's polarity and distribution thereof is therefore useful information in understanding and creating biological activity.

In ligand-based drug design and other biochemical uses of complementarity, the underlying assumption is that a particular known biologically-active compound is complementary in shape and electrostatic potential to the desired target receptor and that the complementarity is responsible for the ligand drug's active effect. Therefore, in ligand-based design, the researcher attempts to locate other compounds having a similar shape and electrostatic potential to the known biologically-active compound in order to capitalize on them and use them as drugs. In receptor-based design, the structure of the target receptor is already generally known in atomic detail, and the goal is to identify compounds that would be complementary to and biologically active with the receptor. Receptor-based design also requires a definition of the binding-site cavity to a degree of detail on the atomic level. Both of these design methodologies therefore rely on an understanding of the shape and electrostatic potential of a particular compound, or the shape of a particular receptor, to locate new molecules having either a similar or complementary shape and electrostatic potential.

A number of methods have been devised for determining an indicator of the shape and electrostatic potential of a molecule or receptor, which can then be compared to other molecules of known shape and electrostatic potential to search for similarities or complements. Current automated programs for comparing receptors and ligands implicitly represent molecular shape via molecular mechanics energy calculations, based on the principle that only molecules that can adopt a shape complementary to a target receptor will result in a favorable binding energy. However, these methods have all met with limited degrees of success in their ability to accurately describe the shape of the molecules or receptors. This limitation on their success is due in part to the fact that they generally hinge on specifying structure. Such reliance on structure is imprecise, because many compounds with radically different composition, structure, and polarity may meet requirements for biological activity. As such, investigators using such methods based on structure must generate multiple queries largely on the basis of imprecise chemical intuition.

Many current methods for designing biologically active molecules require too much information to generate a molecule's shape. Large amounts of input information require undesirable amounts of calculation and input time. It also limits the program's use to investigators with specialized knowledge. One such computer program is Comparative Molecular Field Analysis, or COMFA™, a product of Tripos, Inc. In COMFA™, the van der Waals and electrostatic fields of molecules are sampled over a grid superimposed on the molecule or receptor site. The values of these fields at the particular grid points are then used as descriptors in a regression model. COMFA™ thus includes both molecular shape and polarity. While the COMFA™ method can generally narrow a range of compounds to those which are generally similar, the COMFA™ method has distinct problems in its application. Firstly, COMFA™ uses an undesirably large amount of explicit information to encode shape, involving many grid points and geometric constraints. COMFA™ also requires the inclusion of an overlaid grid on the molecule, which generates questions of accuracy due to the effects of grid spacing and orientation of the molecules being compared.

Other ligand-based methods include the various methods for defining pharmacophore models. These implicitly represent ligand shape by incorporating some collection of hydrogen bond acceptors and donors and regions of steric bulk, and imposing inter-group distance constraints thereon. This three dimensional geometric information thus also requires a large amount of implicit information to provide the shape.

Other approaches attempt to compute topological descriptors of molecules, beginning with chemical structure or the wave function. These also often derive directly from the molecular shape. Further, methods based on chemical fingerprints generally also include implicit shape information, since only a restricted family of compounds will be compatible with the information contained in the fingerprint.

Receptor-based design strategies generally involve an explicit representation of shape derived from an atomic resolution structure of the active site. For example, UCSF DOCK methods pack the active site with spheres, producing an efficient representation of the volume available to accommodate a ligand, and combine this with positions of hydrogen bond acceptors and donors. Other docking algorithms such as FLOG, GOLD and FlexiDock use an all-atom representation of the active site, and thus represent its geometry in fine detail. Pharmacophore-like models can also be devised for receptors, and these include shape information in the same way as ligand-based models.

Thus, all of these ligand- and receptor-based programs rely undesirably on representations of structure and/or require an undue amount of informational input. It is therefore desirable for programs designing biologically active molecules to do so without relying on structure or massive amounts of input information. In addition, the information produced by current methods is difficult to efficiently encode and to use in database searching. Current methods such as those described above demand considerable computation, involving energy or distance-geometry calculations, reliance on data-rich explicit shape representations, and, oftentimes, manual alignment of ligands and receptors. For example, COMFA™ and pharmacophore methods use a large amount of explicit information to encode shape, involving many grid points or geometric constraints. The current systems match a compound to a receptor site or pharmacophore via some sort of computational simulation, involving a genetic algorithm, Monte-Carlo method, or other technique for randomly generating orientations and configurations of the ligand. COMFA™ is also problematically subjective in its requirement of alignment of the series of molecules, and is limited to scanning around 150 compounds. Further, scanning a chemical library with a pharmacophore query involves a significant amount of computation, since each molecule must be repositioned and flexed in order to determine if it can fit the model. Similarly, receptor-based strategies require many packed spheres and/or atom positions to encode the shape of the active site, and rely on scanning a chemical library with a docking program which requires many detailed calculations for each compound considered. These calculations can involve molecular mechanics computations or, at the very least, so-called "bump checks" to test shape compatibility between receptor and ligand.

All of these computations take undesirably large amounts of time and processor resources. They also require an undesirable amount of training time in chemical structure, the docking process, and many other areas; this time corresponds to often scarce financial resources. While improved efficiency in search methods has made approaches usable for screening existing chemical libraries, there is clearly no upper limit on the number of compounds that researchers would like to compare in the pursuit of new biologically active compounds. Further, the faster, and more effectively, a database can be searched, generally the faster a new and useful compound can be discovered.

It is therefore desirable to have a method that can rapidly compare shapes of large databases of compounds to each other, or to a receptor site, with minimal computation and without reliance on chemical structure, explicit 3D representations of shape, or actual ligand-receptor docking. It is further desirable that this method require no special training in chemical structure or docking. Some inroads into this methodology are illustrated by Zauhar et al., Issues and Applications in Toxicology and risk Assessment Meeting, April 2001; and Zauhar et al., ACS National Meeting, August 1999, the disclosures of which are both incorporated herein by reference.

Current methods are also not sufficiently precise for larger molecules and molecules with a variety of functional groups. This is because the attributes of different parts of a large molecule tend to cancel each other out in an analysis of the entire molecule, resulting in a featureless distribution that merely reflects the molecule's rough overall geometry. It is therefore desirable for a comparison method to be accurately applicable to large molecules and molecules with a variety of functional groups.

SUMMARY

Because of these and other problems described herein, and other issues known by those in the art, set forth herein are systems and methods related to the use of what are called "shape signatures" for compactly representing molecular shape and electrostatic potential, and how shape signatures can be used in both ligand-based and receptor-based molecular design. The systems and methods generally use ray-tracing to explore the volume and polarity interior to a ligand, or the space exterior to a receptor site. Probability distributions derived from the ray-traces are generated, and described herein as shape signatures. Shape signatures can serve as compact descriptors of shape and other properties requiring modest storage space, and which may be quickly compared to test for similarity or complementarity.

Both the basic implementation of shape signatures, which include only shape information, as well as extensions that couple the existing ray-tracing technique with other computed molecular properties to define shape signatures with higher-dimensional domains include methods discussed herein. There is also illustrated an approach that includes the molecular electrostatic potential (MEP) to define a two-dimensional (2D) shape signature. These MEP-based 2D shape signatures combine shape and polarity information, and can be used to select molecules that are similar in shape and electrostatic potential to a query.

There is described herein, among other things, a method for generating a shape signature representative of a molecular shape, the method comprising: providing a visualization of a molecule formed of a plurality of atoms wherein said molecule has a determined solvent-accessible molecular surface; dividing said molecular surface into a plurality of small area elements; performing a ray-trace on said visualization, said ray-trace comprising: starting an initial ray at a start point in a first of said small area elements; propagating said ray in a first direction until said ray impacts a second of said small area elements at an impact point, resulting in an initial ray segment between said start point and said impact point; recording characteristics of said initial ray segment; repeating said starting, propagating, and recording for a new ray segment using said impact point of the prior iteration as said start point of the next iteration wherein said first direction associated with said new ray segment comprises the direction of reflection of said initial ray segment from said impact point as if said initial ray segment had propagated from said start point to said impact point; stopping said repeating prior to recording if a predetermined stop condition is met; if stopped, continuing said repeating by restarting said new ray segment at said impact point of said prior iteration, but with a second direction different from said first direction; and finishing said ray trace once a preselected number of ray segments or reflections have been recorded; computing a probability distribution based on said characteristics, said probability distribution providing an indication of said molecule's shape; storing said probability distribution for later comparison to other probability distributions indicative of the other molecules' shape; and comparing said probability distribution to said other probability distributions, relying on a metric.

In an embodiment of the method the other probability distributions are in a database. In another embodiment the predetermined stop condition comprises said first ray or a second ray and a subsequent ray reflecting at a same atom; said first ray or said new ray glancing off said impact point such that said reflection may not be calculated; or said first ray or said new ray failing to strike said impact point. In a still further embodiment, the method further comprises a step of segment culling.

There is also described herein, a method for determining molecular shape and electrostatic potential comprising: having a first molecule with a determined solvent-accessible molecular surface which can be visualized by a processor; visualizing said molecular surface as a plurality of small area elements; said processor performing a ray-trace, said ray-trace comprising: starting a ray at a start point in a first of said small area elements; propagating said ray in a first direction until said ray impacts a second of said small area elements at an impact point, resulting in an initial ray segment between said start point and said impact point; reflecting said ray from said impact point as if said molecular surface was perfectly reflective of said ray; recording characteristics of said ray segment, including electrostatic properties of said impact point and said start point; and repeating said steps of starting, propagating, reflecting, and recording for a new ray segment using said impact point as said start point of said new ray segment; and stopping said repeating prior to recording if a predetermined stop condition is met; computing a probability distribution based on characteristics of said ray, said probability distribution providing an indication of said molecule's shape and electrostatic potential, wherein said probability distribution comprises a reduced histogram; and storing said probability distribution, and said impact points and said characteristics, for later comparison to other probability distributions indicative of other molecules' shapes.

In an embodiment of the method the other probability distributions are in a database. In another embodiment the predetermined stop condition comprises said first ray or a second ray and a subsequent ray reflecting at a same atom; said first ray or said new ray glancing off said impact point such that said reflection may not be calculated; or said first ray or said new ray failing to strike said impact point. In a still further embodiment, the method further comprises a step of segment culling.

There is also described herein, a method for determining molecular shape comprising: having a first molecule with a determined solvent-accessible molecular surface which can be visualized by a processor, wherein said molecule is relatively large or contains varied functional groups; visualizing said molecular surface as a plurality of small area elements; said processor performing a ray-trace, said ray-trace comprising: starting a ray at a start point in a first of said small area elements; propagating said ray in a first direction until said ray impacts a second of said small area elements at an impact point, resulting in an initial ray segment between said start point and said impact point; reflecting said ray from said impact point as if said molecular surface was perfectly reflective of said ray; recording characteristics of said ray segment, including electrostatic properties of said impact point and said start point; and repeating said steps of starting, propagating, reflecting, and recording for a new ray segment using said impact point as said start point of said new ray segment; and stopping said repeating prior to recording if a predetermined stop condition is met; storing said start points and said impact points and attributes of atoms associated thereto; corresponding said initial ray segment and said new ray segment to said atoms; partitioning said molecule into atom clusters; decomposing said ray trace by assigning said initial ray segment and said new ray segment according to results of said step of corresponding, wherein each said ray segment is assigned at least in fractional part to at least one segment corresponding to an atom cluster (an intra-cluster segment) or atoms between atom clusters (an inter-cluster segment); computing a unique probability distribution for each said intra-cluster segment and each said inter-cluster segment based on characteristics of said assigned ray segments, said probability distribution providing an indication of the shape of said inter-cluster segment or said inter-cluster segment; and storing said probability distribution for later comparison to other probability distributions indicative of shapes of other molecules or portions thereof.

In an embodiment of the method the other probability distributions are in a database. In another embodiment the predetermined stop condition comprises said first ray or a second ray and a subsequent ray reflecting at a same atom; said first ray or said new ray glancing off said impact point such that said reflection may not be calculated; or said first ray or said new ray failing to strike said impact point. In a still further embodiment, the method further comprises a step of segment culling.

In a still further embodiment of the method, the probability distribution further provides an indication of said intra-cluster segment's or said inter-cluster segment's electrostatic potential.

There is also described herein, a method for determining molecular shape comprising: having a first molecule with a determined solvent-accessible molecular surface which can be visualized by a processor, wherein said molecule is relatively large or contains varied functional groups; visualizing said molecular surface as a plurality of small area elements; said processor performing a ray-trace, said ray-trace comprising: starting a ray at a start point in a first of said small area elements; propagating said ray in a first direction until said ray impacts a second of said small area elements at an impact point, resulting in an initial ray segment between said start point and said impact point; reflecting said ray from said impact point as if said molecular surface was perfectly reflective of said ray; recording characteristics of said ray segment, including electrostatic properties of said impact point and said start point; and repeating said steps of starting, propagating, reflecting, and recording for a new ray segment using said impact point as said start point of said new ray segment; and stopping said repeating prior to recording if a predetermined stop condition is met; storing said start points and said impact points and attributes of atoms associated thereto; corresponding said initial ray segment and said new ray segment to said atoms; partitioning said molecule into atom clusters; decomposing said ray trace by assigning said initial ray segment and said new ray segment according to results of said step of corresponding, wherein each said ray segment is assigned at least in fractional part to at least one segment corresponding to an atom cluster (an intra-cluster segment) or atoms between atom clusters (an inter-cluster segment); computing a unique probability distribution for each said intra-cluster segment and each said inter-cluster segment based on characteristics of said assigned ray segments, said probability distribution providing an indication of the shape of said inter-cluster segment or said inter-cluster segment; storing said probability distribution for later comparison to other probability distributions indicative of shapes of other molecules or portions thereof, wherein said other probability distributions are in a database; and distinguishing said other molecules by chirality and stereoisomerism.

There is also described herein, a method for determining molecular shape of a receptor comprising: having a first molecule with a determined solvent-accessible molecular surface solvent-accessible molecular surface, wherein said surface is a receptor which can be visualized by a processor; restricting said surface to said receptor's active site; visualizing said molecular surface as a plurality of small area elements; said processor performing a ray-trace, said ray-trace comprising: starting a ray at a start point in a first of said small area elements; propagating said ray in a first direction until said ray impacts a second of said small area elements at an impact point, resulting in an initial ray segment between said start point and said impact point; reflecting said ray from said impact point as if said molecular surface was perfectly reflective of said ray; recording characteristics of said ray segment, including electrostatic properties of said impact point and said start point; and repeating said steps of starting, propagating, reflecting, and recording for a new ray segment using said impact point as said start point of said new ray segment; and stopping said repeating prior to recording if a predetermined stop condition is met; storing said start points and said impact points and attributes of atoms associated thereto; corresponding said initial ray segment and said new ray segment to said atoms; partitioning said molecule into atom clusters; decomposing said ray trace by assigning said initial ray segment and said new ray segment according to results of said step of corresponding, wherein each said ray segment is assigned at least in fractional part to at least one segment corresponding to an atom cluster (an intra-cluster segment) or atoms between atom clusters (an inter-cluster segment); computing a unique probability distribution for each said intra-cluster segment and each said inter-cluster segment based on characteristics of said assigned ray segments, said probability distribution providing an indication of the shape of said inter-cluster segment or said inter-cluster segment; storing said probability distribution for later comparison to other probability distributions indicative of shapes of other molecules or portions thereof.

In an embodiment the method further comprises generating a target volume that functionally corresponds to said receptor, wherein said step of generating utilizes physical surface tension or scaling said ray segment and said new ray segment.

BRIEF DESCRIPTION OF THE DRAWINGS

FIG. 4A has only 100 reflections. FIG. 4B has 10,000 reflections.

FIG. 5A has 10,000 reflections. FIG. 5B has 50,000 reflections.

FIG. 7A uses 10,000 reflections. FIG. 7B uses 50,000 reflections.

FIGS. 10A and 10B for score distributions for Example 3 using a logarithmic axis. FIG. 10A is for a 1D shape signature. FIG. 10B is for a 2D shape signature. Both utilize the $L_1$ metric.

FIG. 11A is for a 1D shape signature. FIG. 11B is for a 2D shape signature. Both utilize the $L_1$ metric.

FIG. 13A corresponds to substituent (103). FIG. 13B corresponds to substituent (105). FIG. 13C corresponds to substituent (107).

FIGS. 14A and 14B provide for results of 1D shape signature comparisons of Tripos fragments using the $L_1$ metric. FIG. 14A is a textual presentation. FIG. 14B provides molecular drawings.

FIG. 15 provides textual results for MEP-based 2D shape signature comparisons of Tripos fragments using the $L_1$ metric.

FIGS. 16A and 16B provide for results of 1D shape signature comparisons of Tripos fragments against the NCI database using the $L_1$ and $R_1$ metrics. FIG. 16A is a textual presentation. FIG. 16B provides molecular drawings.

FIGS. 17A and 17B provide for results of MEP-based 2D shape signature comparisons of Tripos fragments against the NCI database using the $L_1$ and $R_1$ metrics. FIG. 17A is a textual presentation. FIG. 17B provides molecular drawings.

FIG. 19 provides an embodiment of a selection of inhibitors constructed using shape signatures and ALMS. Energies are after 1000 steps (max.) minimization with MaxiMin2, and correspond to a binding-energy estimate as described below.

FIG. 20 depicts an embodiment of triangulating molecular surfaces that uses a physical surface-tension model.

DESCRIPTION OF PREFERRED EMBODIMENT(S)

Figure 1:
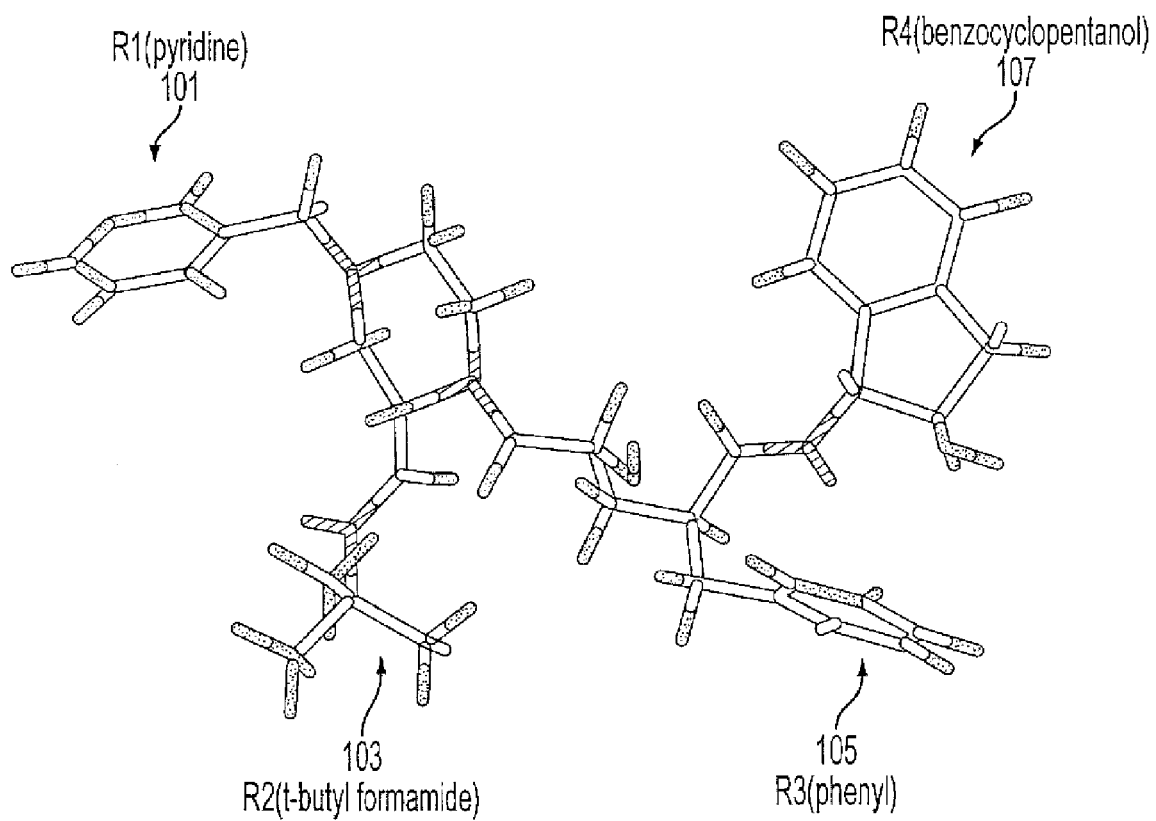
FIG. 1 provides a depiction of the structure of Indinavir, including the substituents used in Example 4.

For the purposes of discussion, the embodiments discussed below will principally be applied to shape signatures for the structure of Indinavir (which is shown in FIG. 1). One of ordinary skill in the art would understand that the systems and methods may be used to determine biologically-active compounds of any type and for use with any receptor or ligand, and the use of HIV Protease and Indinavir as exemplary embodiments should in no way be taken as a limitation on the invention.

One of ordinary skill in the art will also recognize that utilizing shape signatures to search a chemical compound library or other database of chemical compounds requires the database to include shape signature information. Such databases may be any known in the art or created in future, including but not limited to the NCI, ZINC, PDB, commercial, or proprietary databases. This disclosure will presume that the utilized database has been updated with shape signature and/or electrostatic complementarity information so as to be useable to perform such a comparison. In particular, the zinc and PDB databases have been equipped with shape signatures. It is recognized that the methods used for determining a shape signature could be used to determine a shape signature of any compound, and that therefore existing compounds and receptors with known characteristics can have those characteristics reflected in a shape signature.

Figure 2:
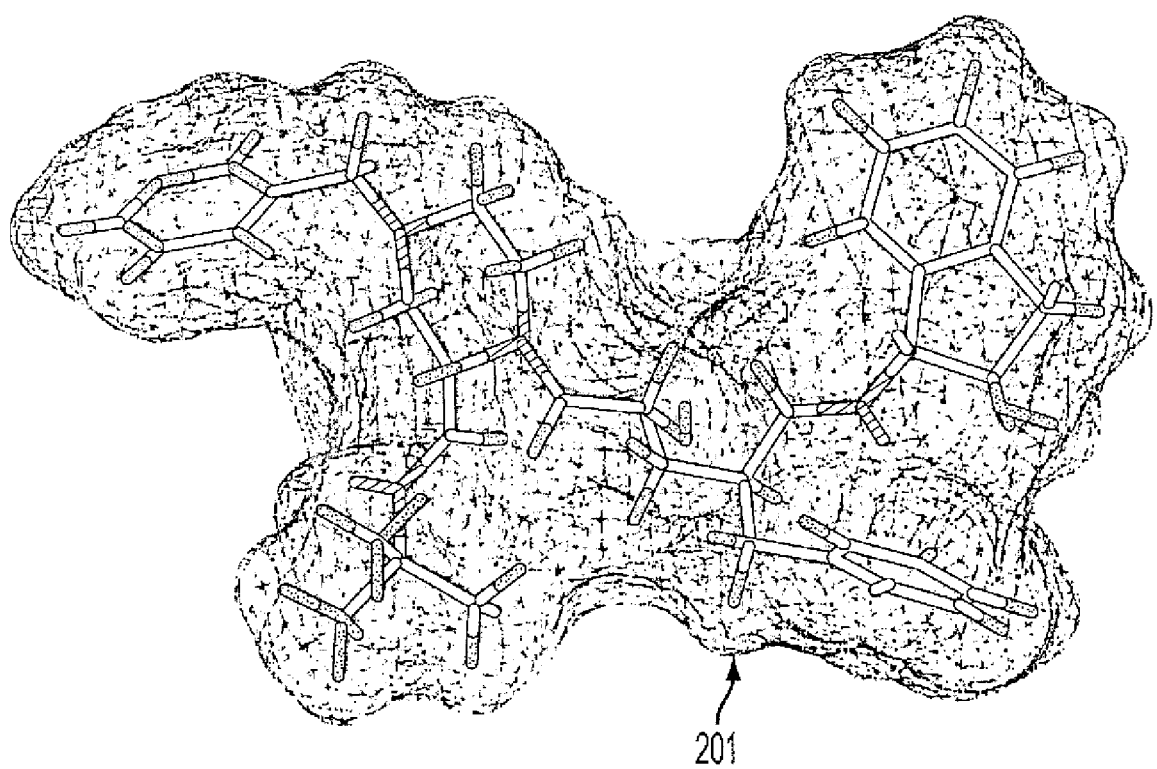
FIG. 2 provides a depiction of the solvent accessible surface of Indinavir which has been triangulated using SMART.

In the shape signatures approach to molecular design, the shape of a molecule is assumed to coincide with its solvent-accessible molecular surface, which may be determined as is known to those of ordinary skill in the art by the points of contact of a rolling spherical probe. As the shape signatures approach preferably uses a detailed representation of the surface, this molecular surface is preferably broken into small area elements. This is preferably accomplished through the use of the Smooth Molecular Surface Triangulator algorithm (SMART) as described in Zauhar, R. J. *SMART: a solvent-accessible triangulated surface generator for molecular graphics and boundary element applications. J. Comput.-Aided Mot. Des.* 1995, 9, 149-159, the entire disclosure of which is herein incorporated by reference. SMART partitions the molecular surface into regular triangular area elements, which are well-suited to the computations that follow. FIG. 2 provides for a representation of Indinavir including the triangulated surface (201) generated using this embodiment.

The definition of the solvent-accessible molecular surface depends upon the choices of atomic radii, solvent probe radius, and the density of element corners (vertices) to be generated. Limiting the input to such rudimentary information allows the methods disclosed herein to require only the most basic information about chemical structure. This permits the methods disclosed herein to be utilized by parties without specialized chemical knowledge. It also permits the methods' application to an almost limitless number and variety of molecular entities, including organics, organometallics, and neutral or charged species.

In an embodiment, the PARSE atomic radii as described in Sitkoff, D.; Sharp, K. A.; Honig, B. *Accurate Calculation of Hydration Free Energies Using Macroscopic Solvent Models. J. Phys. Chem.* 1994, 98, 1978-1988, the entire disclosure of which is herein incorporated by reference, is used. In that embodiment, the radius for the solvent probe is selected to be 1.4 Å, and vertices are spaced approximately 0.5 Å apart. One of ordinary skill in the art would understand, however, that alternative values, models, and selections can be used in alternative embodiments of the invention. In embodiment[s], values for these parameters are automatically assigned default values, and/or may be adjusted by a user.

The volume defined by the molecular surface is explored using a modified form of ray-tracing. Ray-tracing is a technique known to those of ordinary skill in the art for computer animation. Ray-tracing in traditional use tracks the paths of light rays that emanate from some number of pre-defined light sources, and which are then reflected by objects in a scene so as to accurately portray lighting and shadow effects in the final animated scene. In its full realization, ray-tracing takes into account the material properties of objects struck by the ray as well as the atmosphere through which the rays travel. Ray-tracing is also rotationally invariant; that is, the data generated is independent of the object's position or orientation.

Figure 3:
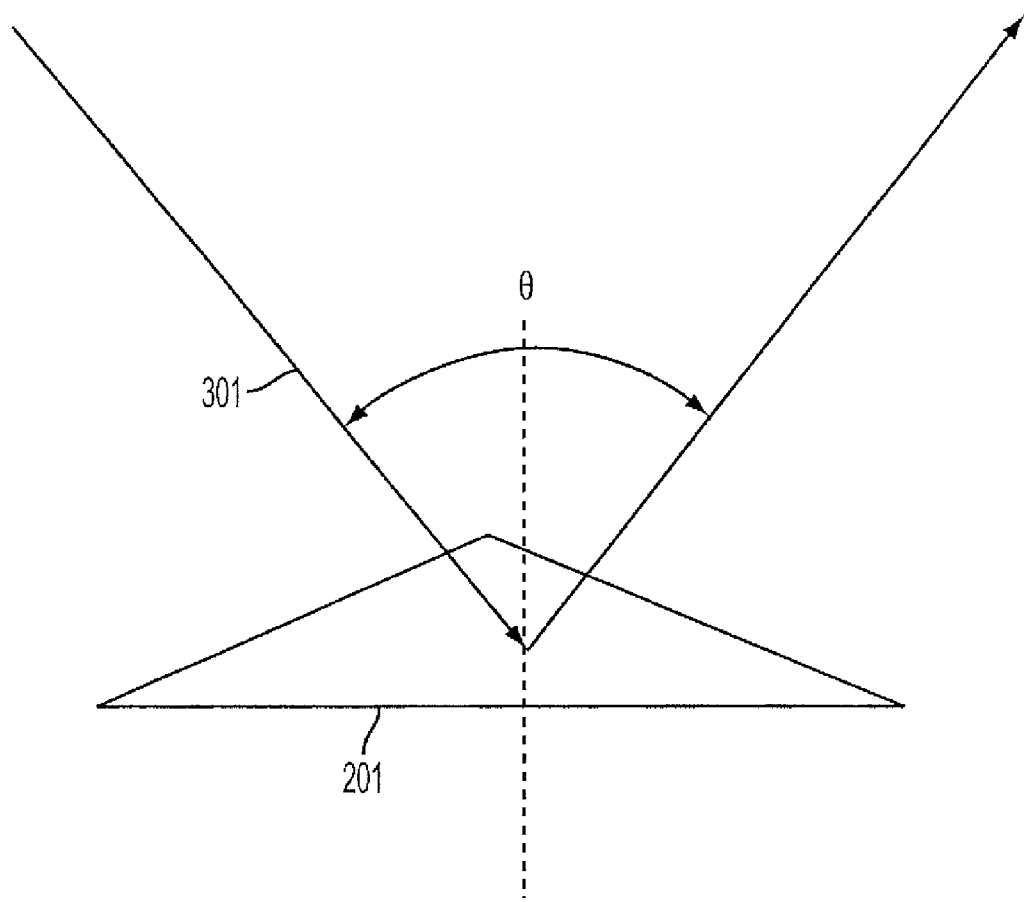
FIG. 3 provides a depiction of the geometry used in a ray-trace. The component of the incoming ray parallel to the plane is unchanged by reflection, while the component perpendicular to the plane is reversed.

In an embodiment of the shape signature application, the ray tracing technique is altered so as to consider only perfect reflection from the molecular surface eliminating any refracting or other imperfect reflection as illustrated in FIG. 3. Further, there are no actual light sources, but rather each light source and light ray is instead a hypothetical source with a source at a randomly-selected point on the molecular surface and a direction in a randomly selected direction. Effectively, the "ray" is a line with a first predetermined source point and a first predetermined direction that is allowed to propagate by the rules of optical reflection when interacting with the molecular surface. Physically, the ray can be thought off as the path of a single photon reflecting on a perfectly reflective complicated surface.

In an embodiment, a ray is initiated at the midpoint of a triangular surface element of FIG. 2, which may be chosen at random or through a particular algorithm, with initial direction defined by selecting a second point at random or via a particular algorithm in a hemisphere centered at the midpoint of the planar element and directing the ray from the first point toward the second point. If the ray-trace is being generated for a ligand or other small molecule, then the hemisphere preferably lies on the interior side of the element as determined by the outward-facing surface normal (which is defined by the SMART algorithm discussed above). If the shape of a receptor site is being defined, then the hemisphere preferably lies on the outward side of the receptor site, and the initial ray propagation is directed toward the exterior of the molecule. One of ordinary skill in the art would understand why these choices are preferably selected. To simply describe, in conjunction with a molecule, the volume is similar to that of a peg (a "solid") whereas for a receptor the volume is similar to that of a hole (a "void").

When performing an exterior ray trace (such as for a receptor), the user preferably supplies a list of atoms that define the receptor site of interest, and only those surface elements that are close to the site atoms are involved in ray propagation, either as initiation points for new rays or as reflection points. Otherwise the ray trace could define an unusable shape signature, in that it encompasses an overly large and irrelevant exterior section of the molecule.

In an embodiment, the exterior ray trace is performed in a manner that takes into account the greater level of detail about the receptor's active site that must be taken into consideration. It is believed that not all areas in a receptor are particularly biologically active, and that the "active site" is responsible for most of the receptor's biological activity. In order to place proper emphasis on information regarding the active site, in a further embodiment, the receptor volume is defined using the residues that line the active site by restricting the ray-trace to the portions of the molecular surface associated with known active-site atoms.

Once a ray is initiated, it is propagated by the rules of optical reflection. That is, the ray (301) effectively forms a beam of light started at the first point and directed in the direction of the second point. The ray (301) continues in a straight path until it hits the surface of the molecule. The ray (301) is then redirected in the direction of reflection from the surface of the molecule, as shown in FIG. 3. The ray (301) then continues again on a straight path until it hits the surface (201) of the molecule where it is again redirected as shown in FIG. 3. This travel and redirection is continued until a predetermined stop condition is obtained. Each time the ray (301) hits the molecular surface (201), the point of impact is recorded or written to a file.

In order to prevent an endless cycle of reflection, and to prevent an endless loop or infinite condition which provides no information, the propagation of the ray (301) is terminated by the occurrence of a stop condition. In embodiment[s] the stop condition is the occurrence of any of the following events: the number of reflections (hits) or ray segments equals a preselected number set by the user; the propagating ray (301) makes a "glancing" contact with a surface element, or strikes too close to the boundary between two adjacent elements to be able to mathematically compute the reflection angle; the ray strikes no surface element and heads out to infinity, a situation occurring in exterior ray-traces; or the contacted surface element and the point of origin are both on the same atom.

Figure 4A:
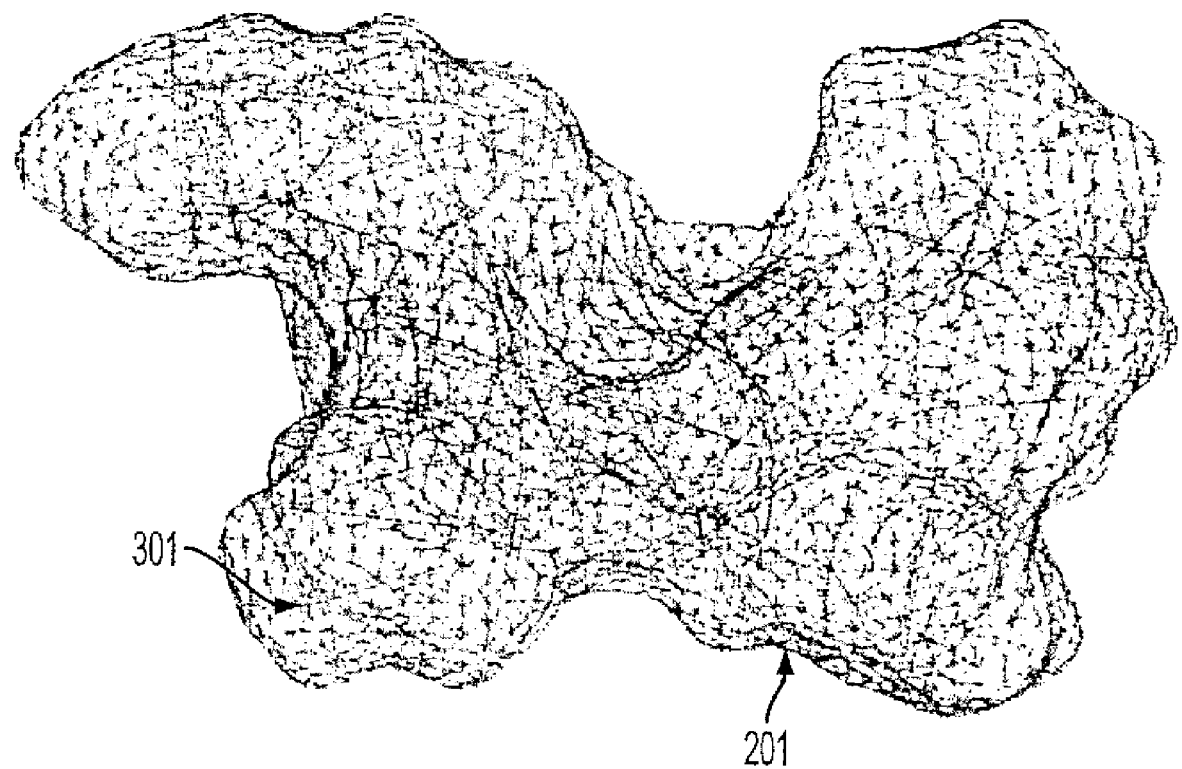
FIGS. 4A and 4B provide for two different ray traces for the surface in FIG. 2.
Figure 4B:
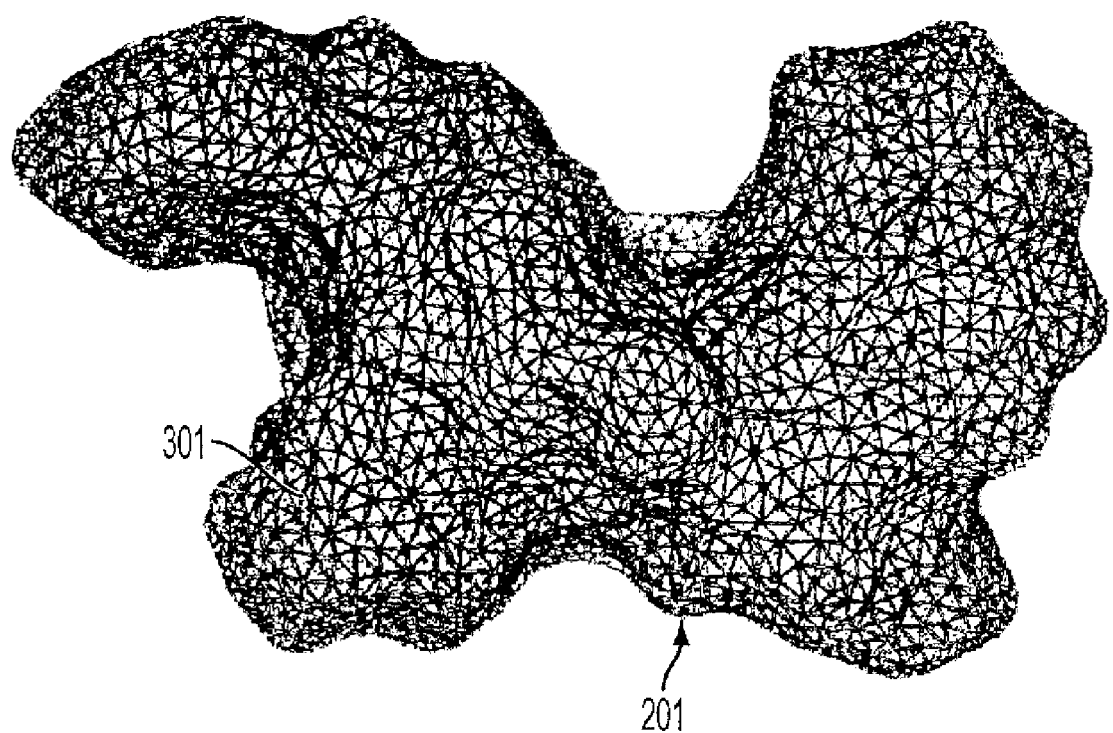

In the first of these situations, the algorithm is finished and the values for the points of impact are recorded. (In an alternative embodiment, the points of impact may be contemporaneously recorded as the ray trace proceeds.) In the other three situations, the ray-trace may be restarted at a newly chosen point and direction on the molecular surface, may be restarted at the same point but with a new direction, may be restarted at a new point with the same direction, or not restarted, in which case the information can be stored and combined with the information from additional rays. In these options, the ray's direction from the newly chosen point may be the direction of reflection as if the ray segment had traveled to that point from the previous impact point. The idea behind the first three of these options is that the ray-trace provides a fixed number of hits by a single path, effectively following a path of total internal reflectance. FIG. 4A shows a first ray-trace for the structure developed in FIG. 2 where the ray (301) has been reflected off the surface (201) 100 times (100 hits). FIG. 4B shows a ray trace for the same structure but with 10,000 reflection points. As can clearly be seen the ray (301) has effectively "filled-in" the inner surface of the surface (201) being no longer even recognizable as a series of lines.

As should be clear from FIG. 4B, the ray-trace provides raw information about three-dimensional shape, particularly by supplying a series of points which are all located on the molecular surface. This raw information is completely independent of surmised chemical structure, and instead relies on and reflects biological properties. As such, ray tracing permits "scaffold hopping," or identifying active molecules that possess similar biological properties but distinct chemical structures. As such, users of the method need not have in-depth knowledge of principles of chemical structure.

While the ray-trace can be useful in itself, in a further embodiment, probability distributions are computed that characterize the ray-trace more compactly and that can then be used as more compact descriptors of shape (and, as discussed later, molecular polarity). "Shape signatures," as that term is used herein, therefore comprise these ray-trace derived probability distributions. For the purposes of this disclosure, the probability distributions (shape signatures) will be represented as histograms, but one of ordinary skill in the art would recognize that other representations (such as, but not limited to, wavelets) may be used in other embodiments, and in fact the abstract mathematical concept may be used without any representation at all in a still further embodiment.

Figure 5A:
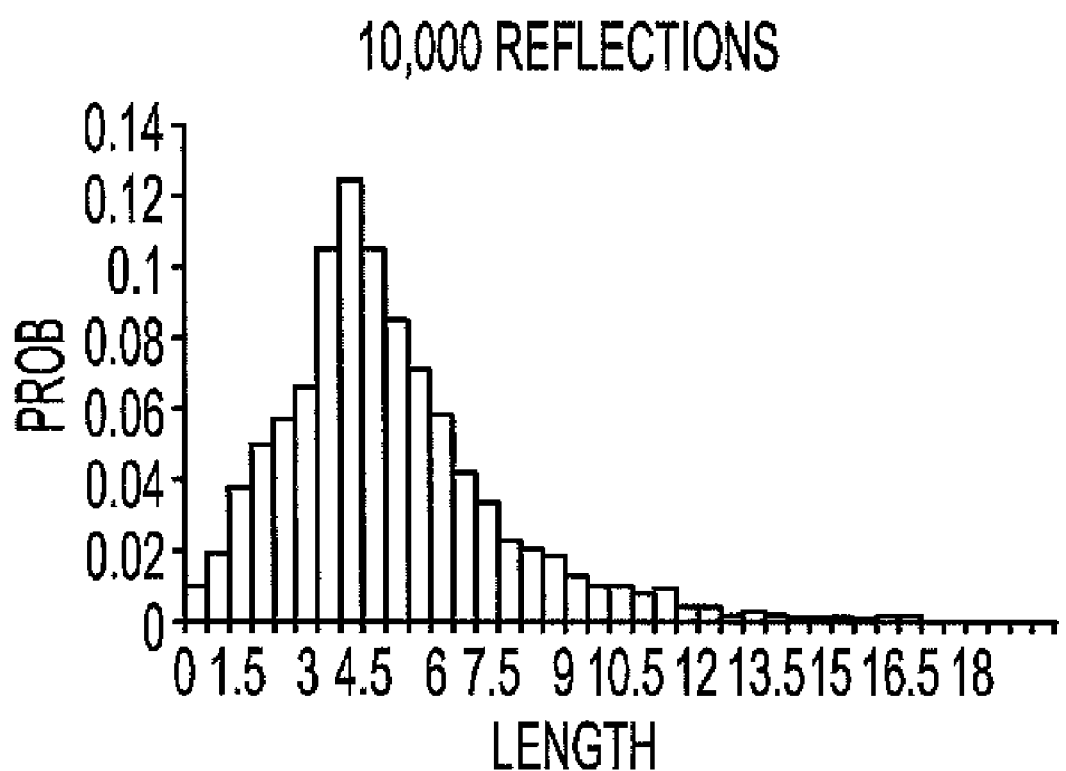
FIGS. 5A and 5B provide 1D shape signatures based on ray-trace segment lengths for Indinavir.
Figure 5B:
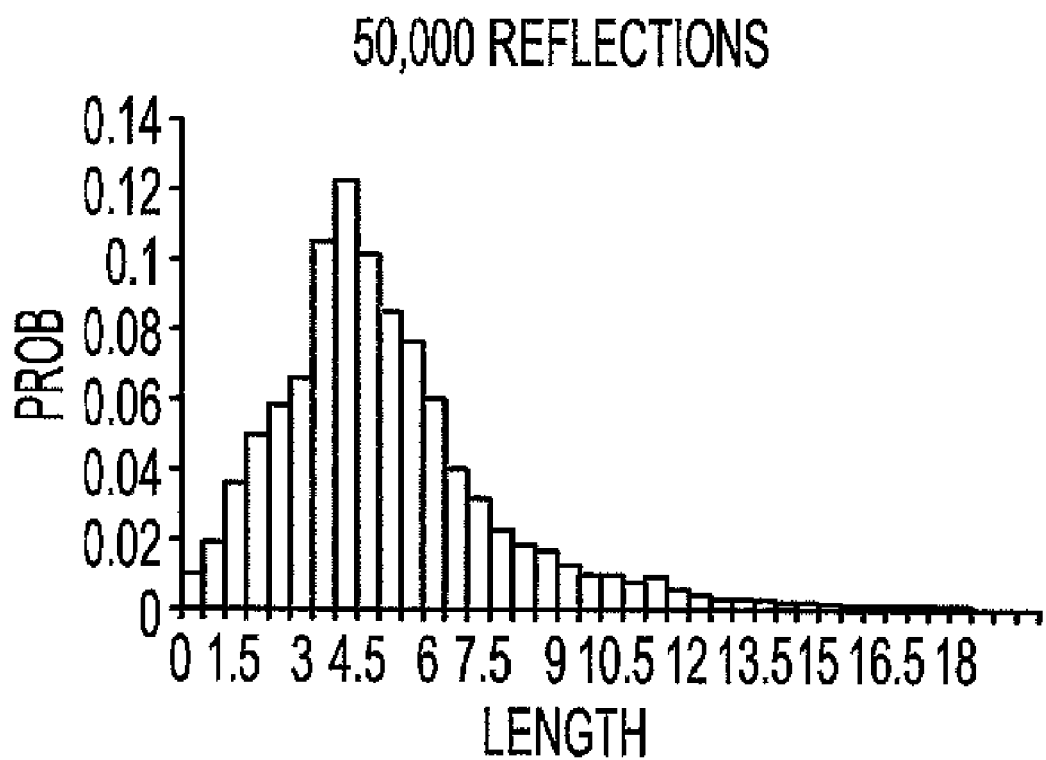

For further purposes of terminology, a line segment of a ray that connects two successive reflection points is called a "ray-trace segment." Perhaps the simplest shape signature is the distribution of the lengths (magnitudes) of these segments. This is called the one-dimensional (1D) shape signature to emphasize that the domain of the probability distribution (namely segment length) has one dimension. FIG. 5 shows the distribution of segment lengths for Indinavir. FIG. 5A shows the distribution derived from a 10,000 point ray trace and FIG. 5B shows the distribution from a 50,000 point ray-trace. It is observed that signatures converge rapidly with increasing number of reflections, and are apparently not sensitive to the initiation point of the ray-trace.

Figure 6:
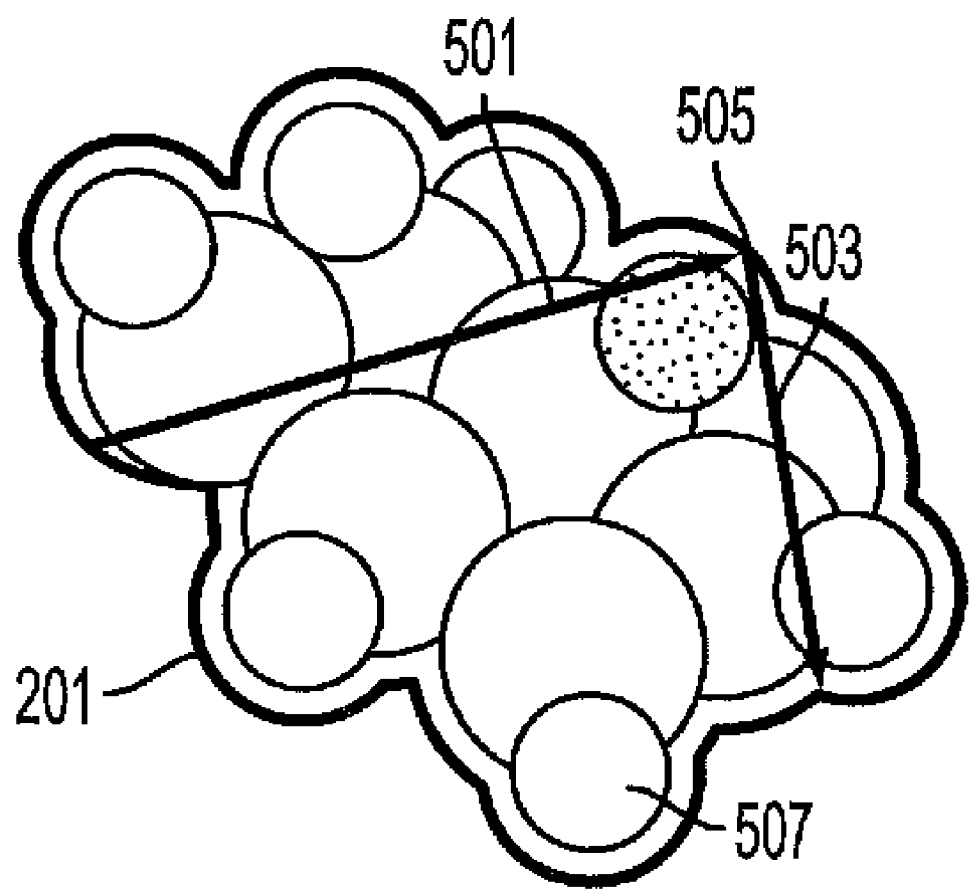
FIG. 6 provides for a representation of an embodiment defining a two-dimensional (2D) shape signature.

In addition to the 1D shape signature, shape signatures can also be defined with higher-dimensional domains (e.g. 2D shape signatures, 3D shape signatures etc.), which incorporate additional molecular descriptors. One approach to generating 2D shape signatures is to associate a surface property measured at each reflection point with the sum of the segment lengths on either side of the reflection. This is shown in FIG. 6 with the length of the first segment (501) summed with the length of the second segment (503) and included with a property of the point (505). One of ordinary skill in the art would see that these examples of 1D shape signatures and 2D shape signatures are merely exemplary and a shape signature can be based on any variable or combination of variables.

Figure 7A:
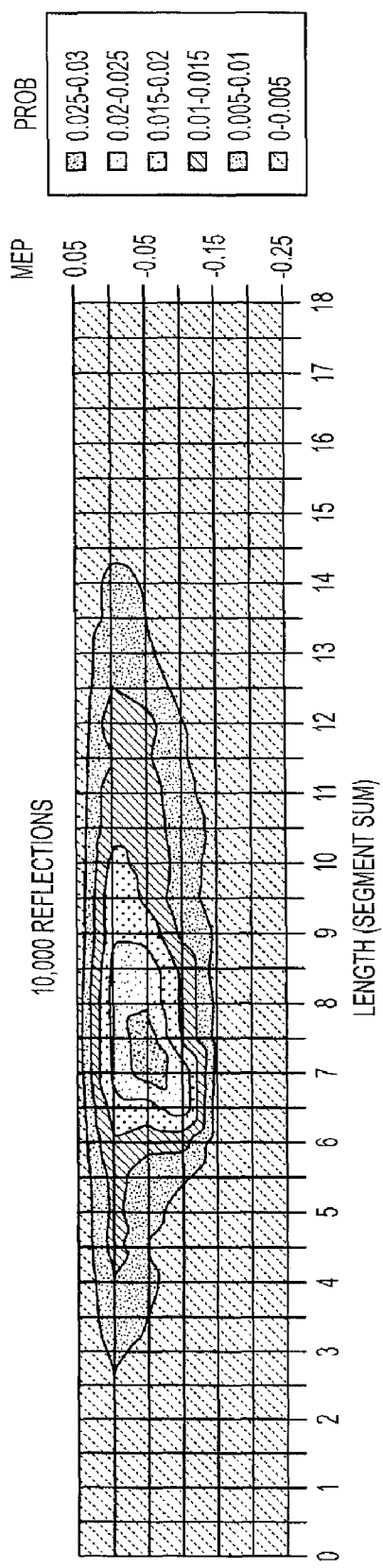
FIGS. 7A and 7B show MEP-based 2D shape signatures for Indinavir.
Figure 7B:
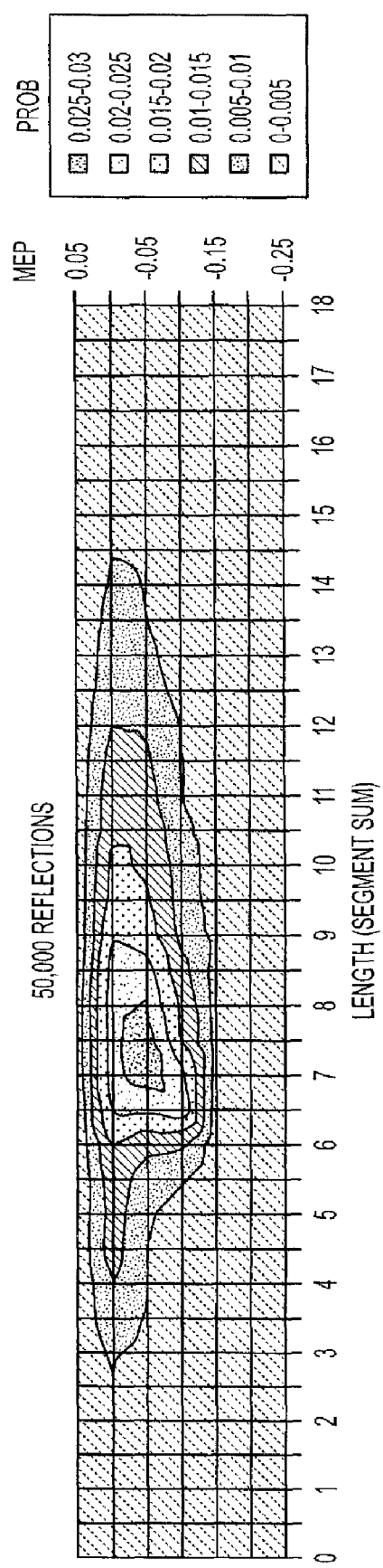

One particularly useful property of a particular reflection point is the molecular electrostatic potential (MEP) of the reflection point. This property is believed to be useful because biological activity is believed, in part, to hinge on the interacting molecules' opposite charge. It is therefore useful to know the charge of a molecule overall and areas thereon believed or desired to be biologically active. This MEP may be obtained through a variety of methodologies, one of which is discussed later in the Examples. FIG. 7 shows MEP-based 2D shape signatures for Indinavir using 10,000 (FIG. 7A) and 50,000 (FIG. 7B) reflections. MEP-based 2D shape signatures are joint probability distributions for observing a sum of segment lengths together with a particular value of the electrostatic potential at a given reflection point. They thus simultaneously encode information concerning shape and polarity.

As should be clear from the figures so far discussed, shape signatures are independent of molecular orientation. This greatly facilitates the method's use. Furthermore, shape signatures require no overlay of a grid on the molecule as they relate instead to internal volume distances and reflection points. This decreases the amount of data input necessary, which in turn expedites execution of the method and makes it useful even to those with limited knowledge or expertise.

The above has detailed how a shape signature can be obtained for any particular relevant molecule. Once shape signatures are obtained, they can be compared to rapidly test for shape similarity between multiple molecules, and shape complementarity between ligands and receptor sites, to perform ligand-based and receptor-based searches.

In an embodiment, shape signatures may be compared by measuring the distance between the associated histograms (shape signatures), using metrics that can be computed quickly. The first metric (equations 1a and 1b) is based on the $L_1$ norm commonly used to compare functions, which may be known as the city-block or Manhattan distance. It is shown in its continuous (1a) and discretized (1b) forms below:

$$L_1(f, g) = \int_D |f(x) - g(x)| dx \tag{1a}$$

$$L_1(f, g) = \sum_{i \in D} |f(x_i) - g(x_i)| \tag{1b}$$

In the use of equation 1a, f and g are functions defined over a common domain D, and the metric function returns a distance between the functions. In an embodiment of the method disclosed herein, equation 1b is used, since, as will be disclosed below, the probability distributions are stored as histograms. It is assumed in this equation that the probability distributions are normalized, so that the sum of the histogram heights over all the bins is unity; then under the $L_1$ metric the maximum distance between two histograms is 2, in which case the histograms being compared have no common support (i.e. no bin positions where both functions simultaneously have non-zero height). The minimum distance between two histograms, under this and most other acceptable distance measures, is zero (corresponding to the case where the distributions being compared are identical). Therefore, the lower the distance measurement generally, the more similar the two shape signatures. This approach may be easily extended to higher dimensions by summing over discretized domains of higher dimension.

The $L_1$ metric provides a measure of the distance between histograms. The absolute value is taken of the difference in the probabilities at corresponding bins (arguments) in the two distributions. The metric is a direct measure of the deviation between the histograms, and is a true metric in the sense that it guarantees useful and important properties such as the triangle inequality (i.e., given histograms A, B, and C, the distance between A and C is less than or equal to the sum of the A-B and B-C distances). The $L_1$ metric works for signatures of any dimension; signatures with a multidimensional domain (e.g., length, angle axes, and electrostatic surface charge distribution) would have that domain divided into bins by a rectangular grid, wherein the index i would index the individual bins, each of which would be characterized by a particular value of length and angle.

Alternatively or additionally, the signatures may be scored according to the Euclidian ($L_2$) metric, set forth below in equation 2:

$$L_2 = \Delta = \sum_i (H_i^1 - H_i^2)^2 \qquad (2)$$

Alternatively or additionally, the signatures may be scored according to the chi squared-based distance set forth below in equation 3, which is known in statistics for comparing discrete distributions:

$$L_3 = \Delta = \sum_i (H_i^1 - H_i^2)^2 / (H_i^1 - H_i^2) \qquad (3)$$

Alternatively or additionally, the signatures may be scored in a manner based on the Bhattacharyya similarity measure, according to equation 4 below:

$$L_4 = \Delta = 1 - \sum_i \sqrt{H_i^1 H_i^2} \qquad (4)$$

The distances $\Delta$ computed between signatures are useful for comparing the shape, polarity, and other surface-mapped molecular properties in diverse applications such as virtual screening of chemical databases, as well as clustering and classification operations in drug discovery and toxicology.

Histogram shape signatures often feature a dominant peak around 3 Å. This arises from ray-trace segments that "measure" small-scale as opposed to large-scale molecular shape. This can be by measuring a small atomic "leg" of the molecule or similar issues. See FIG. 8. In an attempt to amplify the sensitivity to overall molecular shape when making comparisons, the following modified metric (equation 5) may be used in another embodiment:

$$R_1 = \sum_i d_i |H_i^1 - H_i^2| \qquad (5)$$

This is called a ramp metric since it weights the ith term in the sum by a ramp function (the length $d_i$ associated with the ith bins of the histograms).

The analogues of the preceding metrics for 2D shape signatures are equations 6 and 7:

$$L_1^{2D} = \sum_i \sum_j |H_{i,j}^1 - H_{i,j}^2| \qquad (6)$$

$$R_1^{2D} = \sum_i \sum_j d_i |H_{i,j}^1 - H_{i,j}^2| \qquad (7)$$

where index i varies over the length indices of the bins, and j varies over the second dimension (which in all the examples provided herein will be an electrostatic potential scale (MEP) as that is the choice in a preferred embodiment).

The shape signatures approach allows comparison using any of these metrics with very little computing time. Most arithmetic in an embodiment will need to be performed on histograms with fewer than 50 bins. 2D shape signatures obviously require more arithmetic operations than 1D signatures to compare, but the computational expense is still limited and still shortened compared to most existing techniques.

Figure 8:
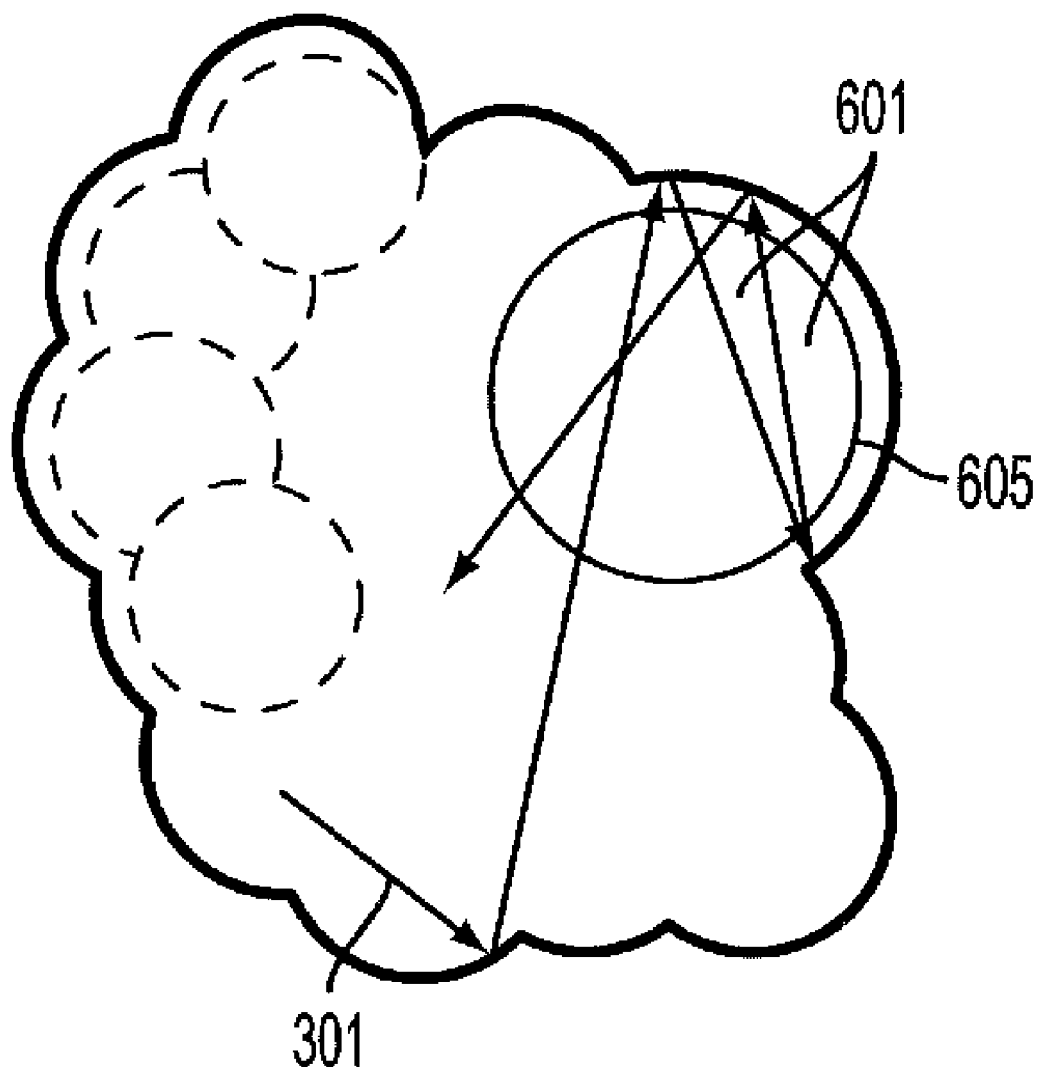
FIG. 8 shows an example of a ray-trace including several segments that span the diameter of a single atom.

It has already been noted that 1D shape signatures will often include a large peak at about 3 Å segment length. Closer examination of the ray-traces from which the shape signatures are derived reveal a large number of segments that span atomic diameters. An example is shown in FIG. 8 where segments (601) essentially span the diameter of atom (605). These segments encode relatively little information about the overall shape of the molecule (simply defining the shape of an atom). Therefore, in an embodiment, the ray-tracing may be modified so that segments that involve reflections at the same atom are discarded. Such reflections may also constitute a stopping condition. In an embodiment, additional segments are then generated as needed to match the user-specified total number of reflections (so as to keep numbers constant). This so-called segment culling helps to ensure that more of the surviving segments encode useful information about the overall shape of the molecule being considered but does entail added computational expense which may or may not be useful in any particular embodiment. Further, a culled shape signature will generally not be comparable to a non-culled shape signature. Therefore, a particular embodiment will generally select whether to use culling or not depending on the intended use and desired comparison of the shape signature.

In use, the shape signatures may be used to identify molecules, molecular fragments, and receptor sites using a relatively simple and easily computable metric. The shape signatures of molecules with known biological effect can then be compared against the shape signatures of other molecules to attempt to find those likely to have a similar biological effect. Alternatively, the shape signature of a receptor may be compared to the shape signature of a multitude of molecules to find molecules which will hopefully bind to the desired receptor.

In an embodiment, shape signatures may be applied to molecular comparison. It is presumed there is an existing database of molecules, which may be saved in any format but is preferably saved in Tripos MOL2 format. From this database of molecules, the ray-tracing procedure may be performed to generate a database of 1D and 2D shape signatures for the molecules. The 2D shape signatures will preferably be MEP 2D shape signatures and the 1D shape signatures single ray-trace segment lengths as discussed above, but that is by no means required. Generally, as will be made clear through description of the embodiments below, the comparison process is advantageous in that it does not require any simulated physical "docking" or "bump check" between the ligand in the receptor. It also does not require intense crunching of large amounts of data. Instead, the comparison method utilizes compact representations of molecular shape and surface charge that may be mathematically compared in a relatively short time period.

To be most useable, and provide for the simplest computation, the molecules in the database preferably have 3D atomic coordinates, and at least partial atomic charges. The atomic charges may be assigned by any method as know to one of ordinary skill in the art, but in the discussed embodiments the Gasteiger method described in Gasteiger, J.; Marsili, M. *Iterative partial equalization of orbital electronegativity—Rapid access to atomic charges. Tetrahedron* 1980, 36, 3219-3288, the entire disclosure of which is herein incorporated by reference, is used.

In a further embodiment, the method disclosed herein comprises a step of distinguishing database molecules by chirality and stereoisomerism. Many current databases do not include multiple representations of the same compound with differing chirality or stereoisomerism; this includes those that utilize simplified molecular input line entry specification, or SMILES, to describe molecules in short ASCII strings. In an embodiment, the method disclosed herein expands SMILES-based (or the functional equivalent) databases to include multiple representations of the same compound. In a further embodiment, where the source strings do not specify tetrahedral and cis/trans isomers, as with the current NCI database, the methods disclosed herein use the CORINA™ (software for generating three-dimensional molecular computer models) program to generate sterically reasonable conformers, and the STERGEN program to generate stereoisomers. The SMILES strings produced in this way can then be processed by CORINA™ or its functional equivalent to generate optimized atomic coordinates for all variants, as disclosed herein. Databases that use isomeric SMILES would not require this step.

Figure 9:
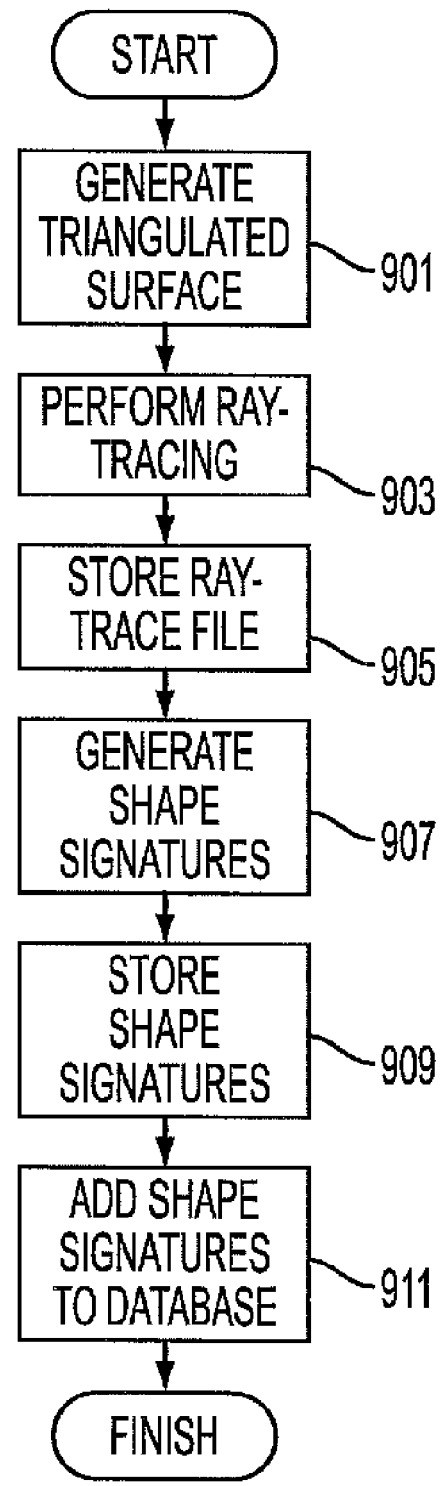
FIG. 9 provides a flowchart for an embodiment of a process for obtaining a shape signature for a molecule.

The ray-tracing and shape signature assignment will generally be performed by a computer or other processor. This may be a standalone workstation, a portable machine, or a client or server located on an interconnected network such as an intranet, an extranet, or the Internet. Further, the term "processor" does not require a single processor, as multiple processors may be used in series or in parallel and still comprise a processor. While the processor will preferably be a general purpose computer including software to perform the desired functions, the processor may also comprise dedicated hardware or software including all special purpose hardware and software. The software may be of any type utilizing any operating system and programmed in any language, but preferably comprises a C-shell script to perform operations of FIG. 9 on the database entry for each molecule.

The processes disclosed herein may be performed relatively quickly. This is due in part to the fact that the step of actually generating the signature need only be performed once, as that information may be stored permanently in a manner linked to the receptor or ligand. This is an improvement over current systems wherein molecular characteristics must be input or derived upon each search. The speed is due also in part to the lean amount of data used in the metrics. On a single 3.5 GHz Intel PENTIUM™ (computer chip) 4 processor, an embodiment of the search methods disclosed herein can generate 1D and 2D-MEP signatures at a rate of 100,000 compounds per day. Alternatively, a cluster of multiple processors permits generating databases of signatures of millions of compounds in a matter of days. Once generated, the databases can be repeatedly searched without reformulation. In addition, the screening process is relatively fast. In an embodiment, identification of closely matching molecules to a query molecule may occur at a rate of approximately one million molecules in thirty seconds, depending on the specific problem.

First, the processor generates a triangulated surface in step (901). This process may be implemented by the script using SMART (discussed above) implemented as a C program. In step (903) the ray-tracing is performed. Generally step (903) will be the most computation intensive step. In order to provide for sufficient speed, a fast algorithm using a grid acceleration method is employed in an embodiment. The algorithm generates a file with a pre-determined number of ray-trace segments which is stored in memory in step (905). The memory may be permanent or temporary, and may be affiliated with the processor or remote from it. In step (907) the histograms or other shape signature information are accumulated by reading the ray-trace file, summing the occurrences of segment lengths, computing the electrostatic potential, or any other steps needed to obtain the shape signatures. The generation of histograms will generally utilize a bin size specified by the user which may be selected by any means known to those of ordinary skill in the art.

To compute the electrostatic potential in step (907), the processor uses, in an embodiment, the partial atomic charges contained in the molecular structure file and equation 8:

$$\Phi(r_p) = \sum_j \frac{q_j}{|r_p - r_j|} \quad (8)$$

where $\Phi(r_p)$ is the molecular electrostatic potential (MEP) computed at reflection point $r_p$ and the index j ranges over all the atoms, which have positions $r_j$ (measured in Å) and partial charges $q_j$ (measured in elementary charge units). The MEP values computed at each reflection point, along with the sum of the segment lengths that adjoin the reflection point, are used to accumulate a MEP-based 2D shape signature as illustrated in FIG. 6.

The resulting histograms are written to a file in step (909) (preferably an ASCII file) in a format that includes all pertinent information in an understandable form. In step (911), another script (which is preferably implemented in PERL™ (computer software)) adds the histogram information to a new database (or alternatively as new entries in the existing database) creating a database including the shape signatures of the various molecules, fragments, and/or receptors.

In an embodiment, the query used to scan the database of shape signatures is itself a database of signatures which could refer to a single object. The query database could be generated from a set of small molecules, in which case the same procedure described above is employed, or a receptor site in a step prior to step (901). In the latter case, the procedure is similar, except that an exterior ray trace is performed (typically over a protein), and the user will specify a set of atoms that define the receptor site. In either case, comparison of the query and target database is effected using a processor, such as that described above, that compares each histogram in the query database against those in the target database using a metric such as one of the ones described above. The processor then reports a hit list file of the best n hits for each of the queries where the variable n is selected by the user or based on particular relevance determinations.

The above described metrics (equations 1-7) can readily compare receptor sites and ligands for shape complementarity; it is less straightforward to measure electrostatic complementarity. However, there are numerous approaches which may be used. One might, for example, simply reverse the sign of the electrostatic field for either query or target signature, and proceed using either of the existing metrics; one then finds an exact match only if query and target signature have exactly complementary shapes, and electrostatic fields that are equal and opposite. Requiring equal charge is an extraordinarily stringent criterion, which would lead to poor scores for clearly useful matches, but can be useful in some situations.

Alternatively, data collected from the ray-trace are binned on the basis of electrostatic potential sign, rather than numerical magnitude. An example of such binning, which results in a histogram that may be referred to as a "reduced" 2D-MEP histogram, is shown in Table 1, below.

age of compounds from the database. While the distributions of scores are of intrinsic interest, as a matter of practice, the user of shape signatures would decide at the outset how many hits to retain in a given search which is a more important limiting factor. Evidence as to the range of scores likely to correspond to close matches is helpful in determining if the number of hits collected was appropriate, but not for much else. The most important observation concerning the distributions is that close matches between compounds are usually found far from the median.

Embodiments of the methods disclosed herein may be tailored to receptors with solvent-accessible active sites. In active sites that are believed to be particularly accessible by solvents, simple ray-tracing may not be effective, because an undesirably large proportion of the rays would be directed out of the active site into infinity, leaving only a small number of rays to poorly define the active site volume. In addition, some active sites bind more loosely to their ligands than others; that is, some active sites and ligands have "wiggle room" between them. For such active sites, it is desirable that the shape signature method take such "wiggle room" into account. In these contexts, an embodiment may generate triangulated molecular surfaces in accordance with a physical surface tension model. Such an embodiment is shown in FIG. 20, applied to the COX-2 receptor; it is contemplated that this embodiment may be applied to any desired receptor. The embodiment begins with a triangulated, approximately

TABLE 1

| MEP \ Length | 0.0 | 2.0 | 4.0 | 6.0 |
|---|---|---|---|---|
| 0.8 | 0 | 0 | 0 | 0 |
| 0.6 | 0 | 15 | 10 | 15 |
| 0.4 | 5 | 25 | 40 | 20 |
| 0.2 | 10 | 20 | 30 | 10 |
| 0.0 |  |  |  |  |
| -0.2 | 20 | 30 | 40 | 20 |
| -0.4 | 30 | 35 | 50 | 30 |
| -0.6 | 20 | 50 | 70 | 15 |
| -0.8 | 0 | 10 | 50 | 0 | to a

|   | 0.0 | 2.0 | 4.0 | 6.0 | 8.0 |
|---|---|---|---|---|---|
| + | 15 | 60 | 80 | 45 |   |
| − | 70 | 125 | 210 | 65 |   |

The probability densities associated with positive potentials in the 2D joint distribution are collapsed into a "+" category for each length value, while all negative bins are collapsed into a "−" category. Two of these transformed histograms corresponding to a receptor and ligand may be compared by inverting the sign of one, by flipping the + and − bin values for each length, and comparing according to a desired metric. If used in comparing ligands to ligands or receptors to receptors, this embodiment may be applied without inverting one histogram's sign. Thusly, a molecule and receptor site with perfect shape complementarity will have a distance of zero, provided that the electrostatic potentials have an opposite sign over the corresponding receptor and ligand surfaces, irrespective of their magnitudes. This less stringent comparison corresponds with the belief that exact electrostatic correspondence is an inappropriately strict criterion for the comparison of receptors and ligands.

It is preferable to have some criteria for assessing the significance of the hit list file produced in a shape signatures search. Scores for 1D and MEP 2D shape signature searches are generally not normally distributed, and it is inappropriate to use z-scores to test for the significance of hits. However, for the queries considered in the examples below, meaningful hits appear in the extreme tail of the distribution, and the typical score cutoffs lead to selection of a very small percentspherical polyhedron that is in a state of constant surface tension, corresponding to the tension exhibited by bulk aqueous solvent. The surface is believed to interact with atoms via a van der Waals potential function. The surface experiences an interior pressure, which is continuously adjusted using a Boyle's Law relationship to achieve a "target volume" for the surface. The initial polyhedron (701) is positioned in the active site. In the embodiment shown in FIG. 20, the initial polyhedron (701) is positioned at the approximate center of the receptor. A target volume is assigned, and the surface (702) is allowed to move (i.e., expand and contract) under the combined effects of interior pressure, surface tension, and steric interactions with atoms, until an equilibrium shape is achieved. This movement is shown as element (702) in the form of inflation to an intermediate volume. Element (703) shows maximal inflation. Thus, the embodiment produces an expanded bubble (703) conforming to the receptor site's shape that can accommodate a ligand of appropriate size. The bubble (703) thus functionally corresponds to the receptor's solvent-accessible surface, in that it represents the surface as it is functionally engaged by the ligand. This bubble (703) minimizes the effect of solvent accessibility: the bubble (703), rather than a ray-trace prone to decreased usefulness in such a context, has a defined target volume. The bubble's (703) defined target volume can be determined given the volume of ligands known to bind to that receptor. In a further embodiment, by adjusting the target volume, the fraction of the receptor site that the bubble (703) occupies can be optimized in order to permit any necessary "wiggle room." The surface obtained by this method is then used in accordance with the ray-tracing methods disclosed herein.

"Wiggle room" may additionally or alternatively be accommodated by an embodiment that scales the lengths of ray-trace segments during histogram assembly. In this embodiment, the entire receptor shrinks by a fixed scale factor, which compensates for void volume effects. That is, a ligand that exactly matches the scaled receptor will also, logically, fit into the full-size receptor, while maintaining a separation from the receptor atoms. Thus, the scale factor corresponds to the amount of "wiggle room" desired. In a further embodiment, the user supplies the factor by which the lengths are to be scaled.

An embodiment of the shape signature method, which may be referred to as "cluster shape signatures," is particularly useful in the context of large molecules or those with varied functional groups. In this embodiment, a ray-trace is generated in the manner disclosed above, and the positions of individual reflections and attributes of the atoms associated with each reflection are recorded. An external program imports the ray-trace data and the atomic coordinate file for the molecule, and associates or matches each reflection point with one or more atoms corresponding to the specific element of the surface triangulation that contained the reflection. The term "external" is used to describe the program's "add-on" or optional nature, rather than any requisite separation from the standard shape signature program. It is contemplated that this external program may be executed on the same or a different processor immediately after or remote in time from generation of the ray-trace. In this way, ray-trace segments (which have a reflection on each end) may be corresponded to sets of one or more atoms on each end. This correlation may be recorded.

The external program next partitions the molecule into atom clusters, which in an embodiment is according to the following algorithm:

1) All bonds that form cycles (rings) are identified using the interatomic connection table generated from the list of bonds in the molecular structure file; these bonds involve only heavy (i.e., nonhydrogen) atoms.

2) Contiguous sets of cyclic bonds are identified; these define the molecule's discrete ring systems, each of which is the core of an atom cluster for the compound.

Figure 21:
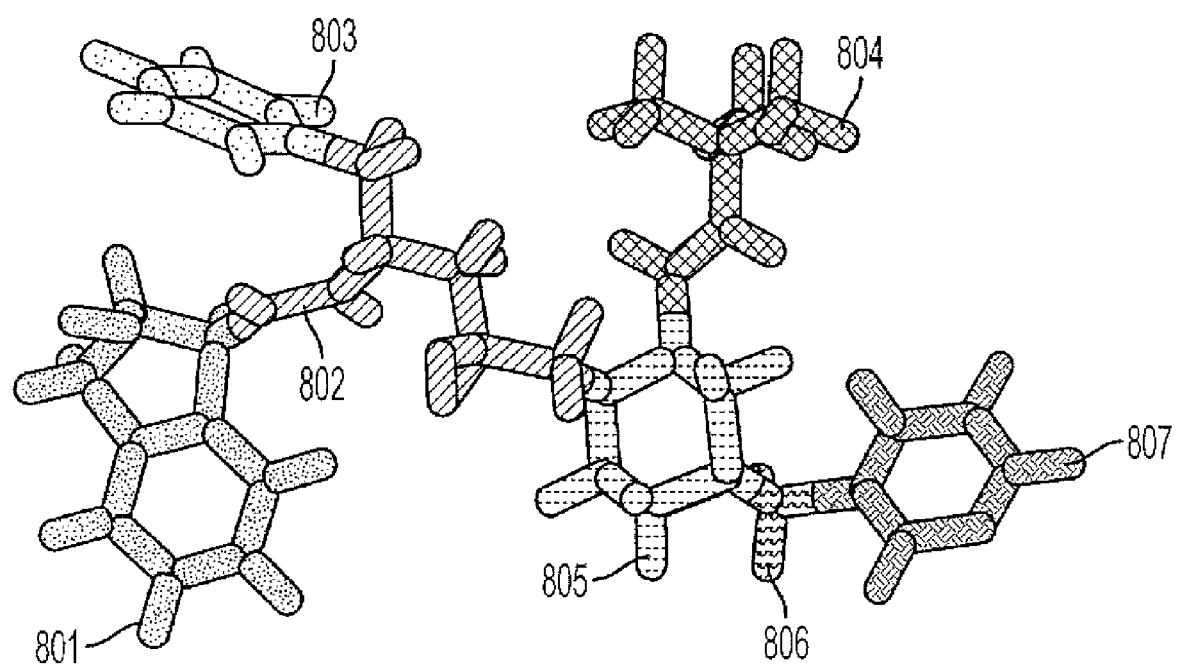
FIG. 21 depicts the clusters identified in an embodiment of a cluster shape signature for Indinavir.
Figure 22A:
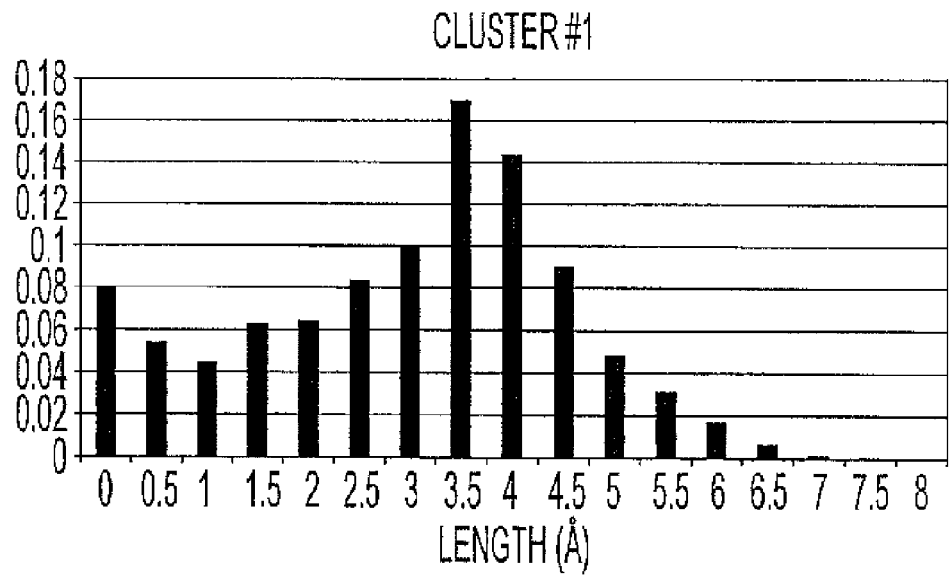
FIGS. 22A, 22B, 22C, and 22D depict some histograms derived from the cluster shape signature for Indinavir.
Figure 22B:
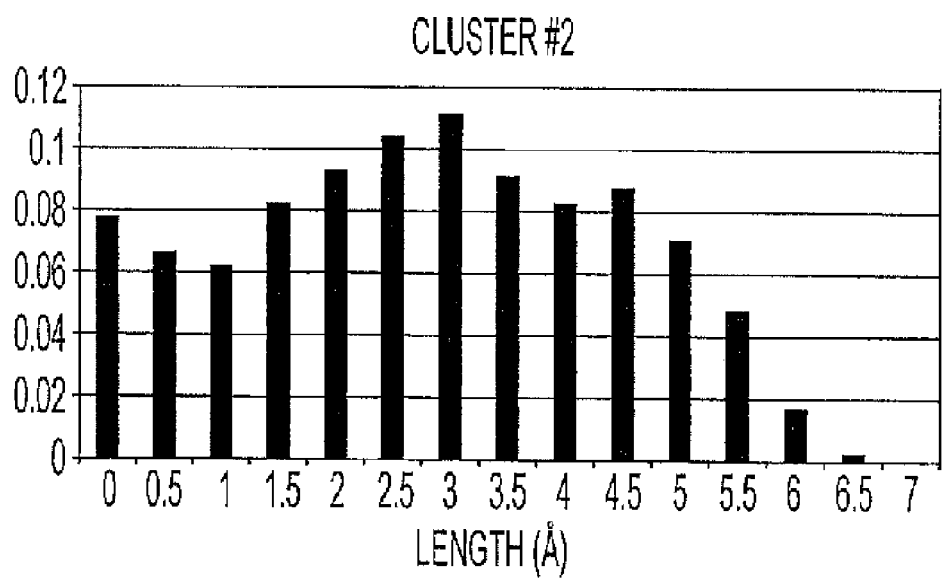
Figure 22C:
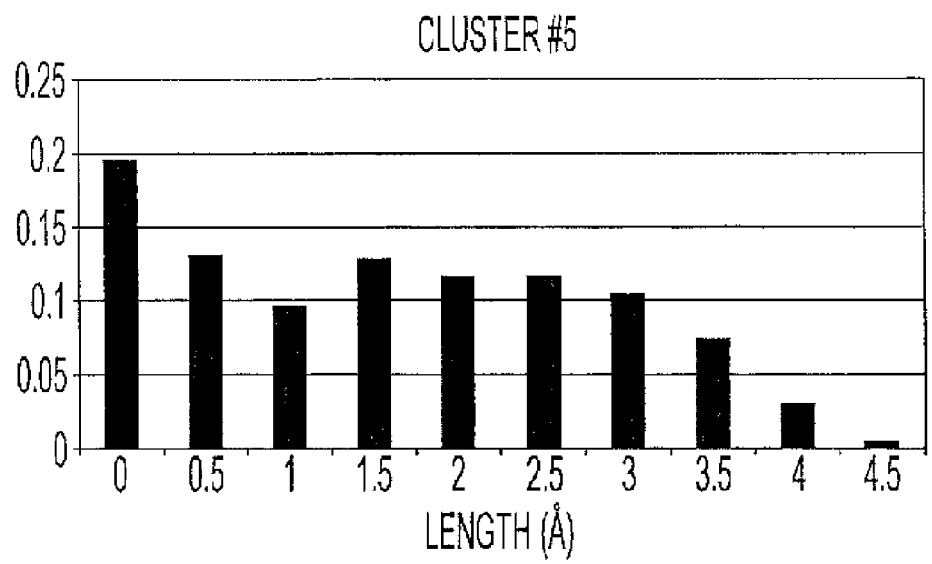
Figure 22D:
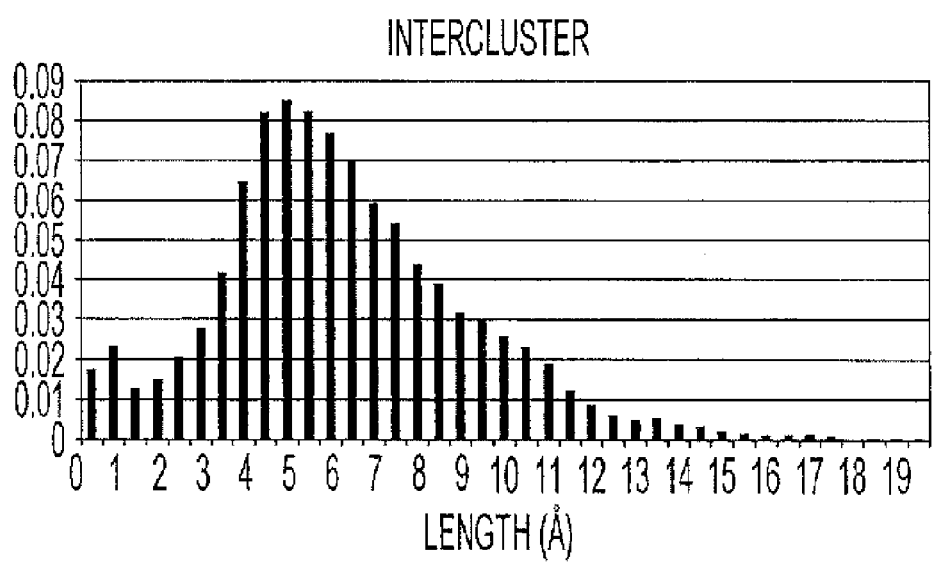

3) Non-cyclic bonds that connect heavy atoms are identified; all contiguous sets of non-cyclic bonds are assembled to form clusters that link to the ring clusters already defined. At this stage, all heavy atoms are assigned to clusters. An embodiment of this step applied to the HIV protease inhibitor Indinavir, resulting in seven clusters (801) (802) (803) (804) (805) (806) (807), is illustrated in FIG. 21.

4) Hydrogen atoms are merged with the clusters of the heavy atoms to which they are bonded.

5) Non-cyclic clusters which are connected to only one cyclic cluster (and thus might form a ring substituent) or which comprise four or fewer atoms are merged with the neighboring cuclic cluster.

Using the cluster assignments generated in step (3), a family of shape signatures is generated by decomposing the ray trace into intra-cluster segments and inter-cluster segments. A separate histogram is generated for each atom cluster using ray-trace segments that connect atoms of the cluster. The intra-cluster segments are assembled into individual, independently-normalized shape signatures which correspond to the compound's component parts as determined by step (3). A single inter-cluster histogram is accumulated for all segments that connect atoms of distinct clusters. The inter-cluster segments are also grouped into a single normalized shape signature, which represents the compound's "glue" holding together the clusters determined by step 3. FIG. 22 shows an embodiment of the shape signatures resulting from application of this method, corresponding to three of the intra-cluster histograms (22A, 22B, and 22C) and the inter-cluster histogram (22D) for Indinavir, generated from a ray-trace with 50,000 reflections. Cluster 2 is cyclic, and cluster 5 is non-cyclic.

Cluster shape signatures may then be compared. All of the intra-cluster signatures of the query may be compared against the intra-cluster signatures of the target, retaining the best match for each cluster. The sum of best scores for the individual clusters is reported, along with the single best score for any cluster; either score can then be used in ranking hits. This comparison method provides flexibility in comparing large molecules, as the user may opt for requiring a close match between multiple clusters, or look for a single close match that may indicate a local similarity between the query and target molecules.

An embodiment of this comparison method is shown in Tables 2 and 3 below, which show the results of using the anticancer therapeutic GLEEVECT™ a query to scan two sets of compounds: one containing molecules known to be closely similar to GLEEVEC™, and the other containing compounds of similar size but unrelated in shape or structure to GLEEVEC™. Table 2 compares average cluster-cluster best-match scores for the "Similar" compound set, along with the scores for the single best cluster-cluster comparison and the scores for the inter-cluster histograms. Table 3 presents the same data for the "Dissimilar" compound set.

TABLE 2

Gleevec ™ Comparisons Against Similar Set

| Name/Code | Ave Cluster-Cluster Score | Best Cluster-Cluster Score | Score for InterCluster Histogram |
|---|---|---|---|
| CID_10295448 | 0.133 | 0.0313 | 0.121 |
| CID_10435761 | 0.115 | 0.0303 | 0.0845 |
| CID_11503240 | 0.141 | 0.0588 | 0.132 |
| CID_11756101 | 0.148 | 0.0409 | 0.104 |
| CID_1261304 | 0.189 | 0.0589 | 0.0850 |

TABLE 3

Gleevec ™ Comparisons Against Dissimilar Set

| Name/Code | Ave Cluster-Cluster Score | Best Cluster-Cluster Score | Score for InterCluster Histogram |
|---|---|---|---|
| CID_16651492 | 0.305 | 0.0921 | 0.105 |
| CID_16717573 | 0.372 | 0.156 | 0.261 |
| CID_16717669 | 0.220 | 0.068 | 0.167 |
| CID_16717694 | 0.248 | 0.105 | 0.218 |
| CID_16717701 | 0.370 | 0.141 | 0.454 |
| CID_16717713 | 0.236 | 0.0780 | 0.120 |
| CID_5058607 | 0.280 | 0.0997 | 0.219 |
| CID_5058608 | 0.226 | 0.0864 | 0.183 |
| CID_553318 | 0.243 | 0.0556 | 0.410 |
| CID_553402 | 0.193 | 0.0834 | 0.502 |

As can be seen, all scores for the "Similar" set are better than the "Dissimilar" set, based on the principle that a score of 0.05 or less is considered a strong indicator of significant shape similarity. Even among the "Dissimilar" set, significant scores are observed for individual cluster-cluster comparisons. Thus, the fact that the comparison provides not only the cluster-cluster score, but also the cluster atoms in each compound, the user can make an immediate comparison of the best cluster. Identified promising clusters can also be retraced, with more extensive ray-tracing or alternate conformers.

It is conceivable that a segment may make fractional contributions to different histograms. As an example, a single ray-trace segment may connect a reflection associated with clusters 1 and 2 to a reflection that is associated with clusters 1, 2, and 3. This segment would contribute as follows: ⅙ to the histogram for cluster 1, ⅙ to the histogram for cluster 2, and the remaining ⅘ to the inter-cluster histogram.

In this manner, cluster shape signatures avoid the "canceling out" on averaging effect of large molecules or molecules with varied functional groups. In addition, subgroups with the potential to be biologically active may be identified even if the molecule as a whole is not believed to be so active.

As a whole, shape signatures is a comparatively easy technique to apply. Particularly for ligand-based applications, the method does not require extensive experience in constructing queries, adjustment of numerous parameters, or sophistication in the interpretation of results, which can be serious drawbacks with other methods. Moreover, it directly addresses those features of molecules, namely their shape and surface properties, which are believed most critical to determining their biological activity. It does so to the exclusion of chemical structure. In this determination, it is also more efficient than previously known methods in its use of computational time and resources.

The shape signatures approach generally does not take into account synthetic feasibility of actually creating the desired molecules or compounds, focusing instead on shapes of even hypothetical structure. Fragments are attached to the framework as discussed in Example 4 with no regard to the existence of a synthetic route for preparing the derivative, and with no regard to the cost or availability of the necessary reagents.

EXAMPLES

Example 1

The shape signatures method was applied to the Tripos fragment database, a diverse collection of small molecules including heterocycles, carbohydrates, amino acids and nucleotides, which is supplied as a standard component of the SYBYL™ (computer program for modeling) molecular modeling package. This database was especially useful for initial tests given its small size and its incorporation of multiple representatives of each family of compound (ensuring that a given query from the database will usually have several potential matches). Very small fragments were removed from the database at the start, and also some perfectly linear molecules (e.g. allene) which were not handled well by the SMART surface algorithm. This left a total of 235 compounds. Dummy atoms were removed from the amino acids in the database and the resulting empty valences filled with hydrogens. The sidechains of glutamic acid, aspartic acid, lysine, and arginine were modified to correspond to the ionized form. Gasteiger charges were assigned to all the compounds in the final set, and 1D shape signatures (utilizing ray-trace segment length) and MEP-based 2D shape signatures were generated using either 50,000 or 250,000 reflections in each ray-trace in separate computational experiments. The shape signatures were then assembled into databases.

Each resulting database was compared against itself (i.e. each compound in the database was used as a query and compared against all the remaining compounds). The $L_1$ and $R_1$ metrics were used in separate comparison. For each query, the ten best (lowest-scoring) hit compounds were retained. This self-comparison was carried out for both the 50,000- and 250,000-reflection databases, using both 1D shape signatures and 2D shape signatures, and with segment culling either enabled or disabled. Examination of the hit compounds in the context of their scores was used to propose score cutoffs to distinguish those matches likely to be interesting.

Figure 14B:
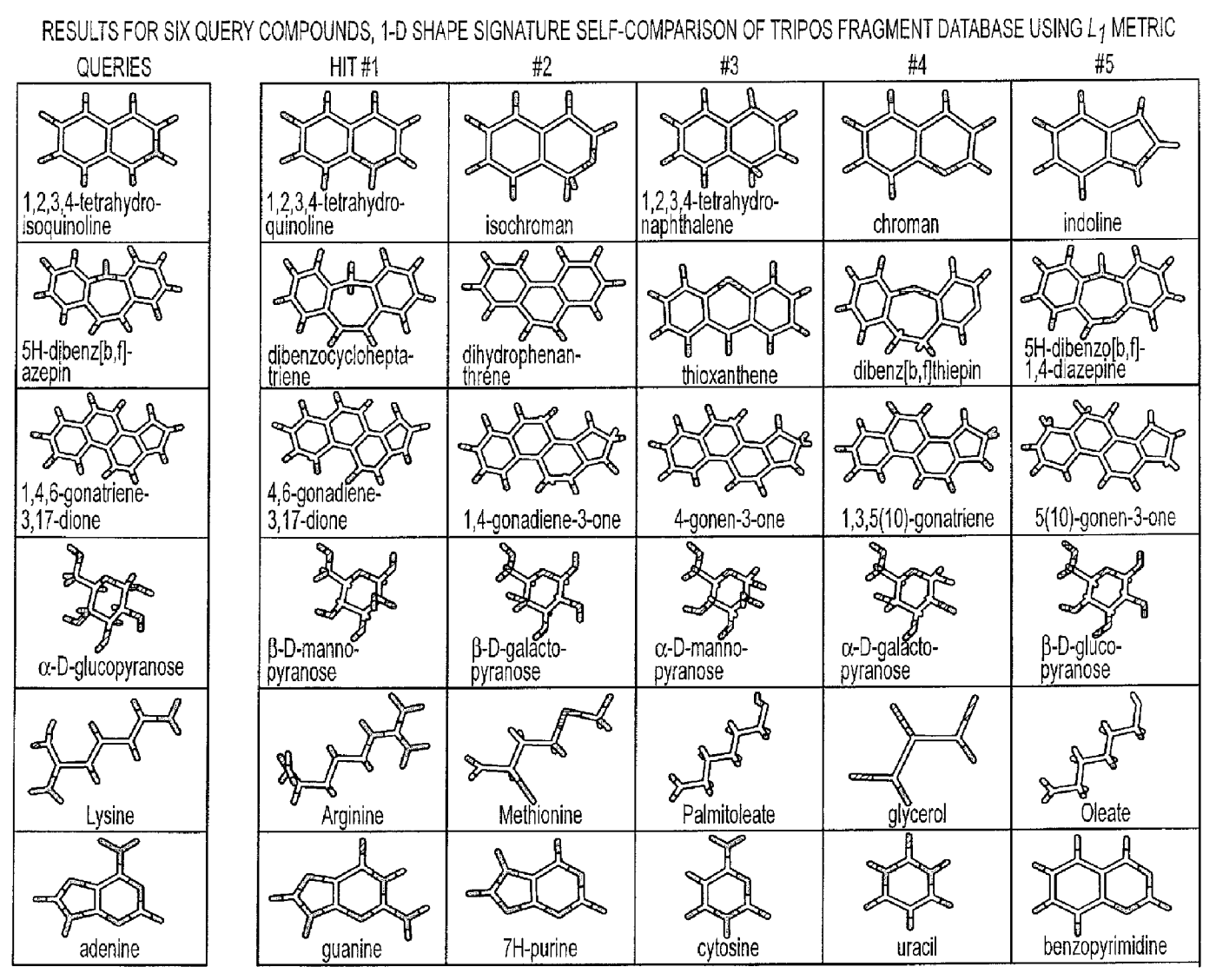

FIG. 14A shows hits found for a selection of query compounds, with 50,000 reflections per histogram using 1D shape signatures and the $L_1$ metric, and with segment culling enabled and disabled. FIG. 14B shows structures of the top five hits for each of the six queries, for the case of segment culling enabled.

In this Example, the 1D shape signatures selected compounds chemically or structurally similar to the query. This observation is amplified by examining all of the available data for the Tripos database. It is believed that one compound of a class generally selects all compounds of the same class present in the database. A fatty acid (laurate) generally selected all other fatty acids present in the database; a carbohydrate (α-dglucopyranose) generally selected other carbohydrates; an amino acid (lysine) generally selected other amino acids; and so on. Dispensing with the segment-culling procedure affects the size of the scores slightly, usually making the distances between histograms a bit smaller, but clearly has little effect on the rank order of hits in this example. Switching to the $R_1$ metric changed the size of the scores, but had little impact on the rank order of hits for most of the queries.

MEP-based 2D shape signatures produced results similar to those of the 1D search, but with some changes in hit ranking that exhibit sensitivity to the electrostatic properties of query and target compounds, and with a much smaller number of meaningful hits. This is not surprising, given that the MEP-based 2D shape signature searches select simultaneously on the basis of shape and polarity, and thus are more stringent than 1D shape signature searches. Examples of this are seen in FIG. 15 for MEP-based 2D shape signatures compared under the $L_1$ metric. For example, where the query "lysine" selected methionine among the top five hits when only shape was considered (FIG. 14A), the 2D shape signature search results do not include this compound. Initial experience with this metric suggests that meaningful 1D shape signature matches between query and target usually involve distances of less than 0.1 probability unit, while useful 2D shape signature hits are within 0.2 of the query.

The results found when comparing the fragment databases prepared using 250,000 reflections per compound were essentially identical to those discussed above, for all combinations of search type (1D or 2D) and metric ($L_1$ or $R_1$). This indicates that 50,000 reflections per compound assure adequate convergence, at least for molecules found in the Tripos fragment database.

CPU times for the Tripos fragment database self-comparison (235 queries, 55,225 comparisons) under the $L_1$ metric on a 1.5 GHz PENTIUM™ (computer chip) processor were 20.5 sec (1D search) and 53.7 sec (2D-MEP search). Timings under the $R_1$ metric were essentially identical. These total times correspond to approximately 370 µsec for a single 1D shape signature comparison, 970 µsec for an MEP-based 2D shape signature comparison.

Example 2

The National Cancer Institute ("NCI") compound database as bundled with the SYBYL™ (computer program for modeling) UNITY tools was used as a source of molecules for creation of a shape signatures database with 1D shape signatures based on ray-trace segment length and MEP-based 2D shape signatures. The starting database was screened for all compounds with molecular weight less than 800 Da, yielding 113,826 molecules. Gasteiger charges were computed for all of the molecules in the resulting working set. 1D shape signatures and MEP-based 2D shape signatures were computed for all the compounds, using a sixteen-processor SCYLD BEOWULF™ (operating system permitting clustering of stand-alone computers) cluster. Each processor was simply allotted a fraction of the molecules to be analyzed, and there was no need to employ the use of parallel code. 50,000 reflections were generated in the ray-trace for each compound, and segment culling was employed, as described above. Of the compounds processed, about 0.4% failed (in every case due to an error in molecular surface generation), yielding a total of 113,331 compounds in the NCI shape signatures database used in subsequent work. Preparation of the database consumed approximately 100 hours wall-clock time on a sixteen-processor cluster of 450 MHz PENTIUM™ III (computer chip) processors running under the Linux operating system.

Example 3

All of the 1D shape signatures and 2D shape signatures (50,000 reflections per signature) generated in Example 1 were used as queries against the NCI shape signatures database generated in Example 2. The best 50 hits for each query were collected. Searches were carried out using 1D and 2D shape signatures, along with either $L_1$ or $R_1$ metrics (Equations. 1-2, and 3-4 respectively) for a total of four searches. Six query compounds, comprising a set that is both structurally diverse and biologically interesting, were selected for detailed examination.

A special concern when comparing a query against a large database is the distribution of scores. To be useful, a search method must exhibit a high degree of selectivity, so that truly interesting hits have scores that differ markedly from the mean. In other words, it should be possible to identify a reasonable cutoff score which can be applied to extract a relatively small and meaningful set of hits from a diverse target database. To examine the character of the scores distribution for shape signatures, a special version of the search program for the $L_1$ metric was prepared which accumulated score statistics in a file. It was thus possible to accumulate the distribution of scores from this relatively large database, and to express the number of observed hits as a function of score for each query molecule.

Figure 16B:
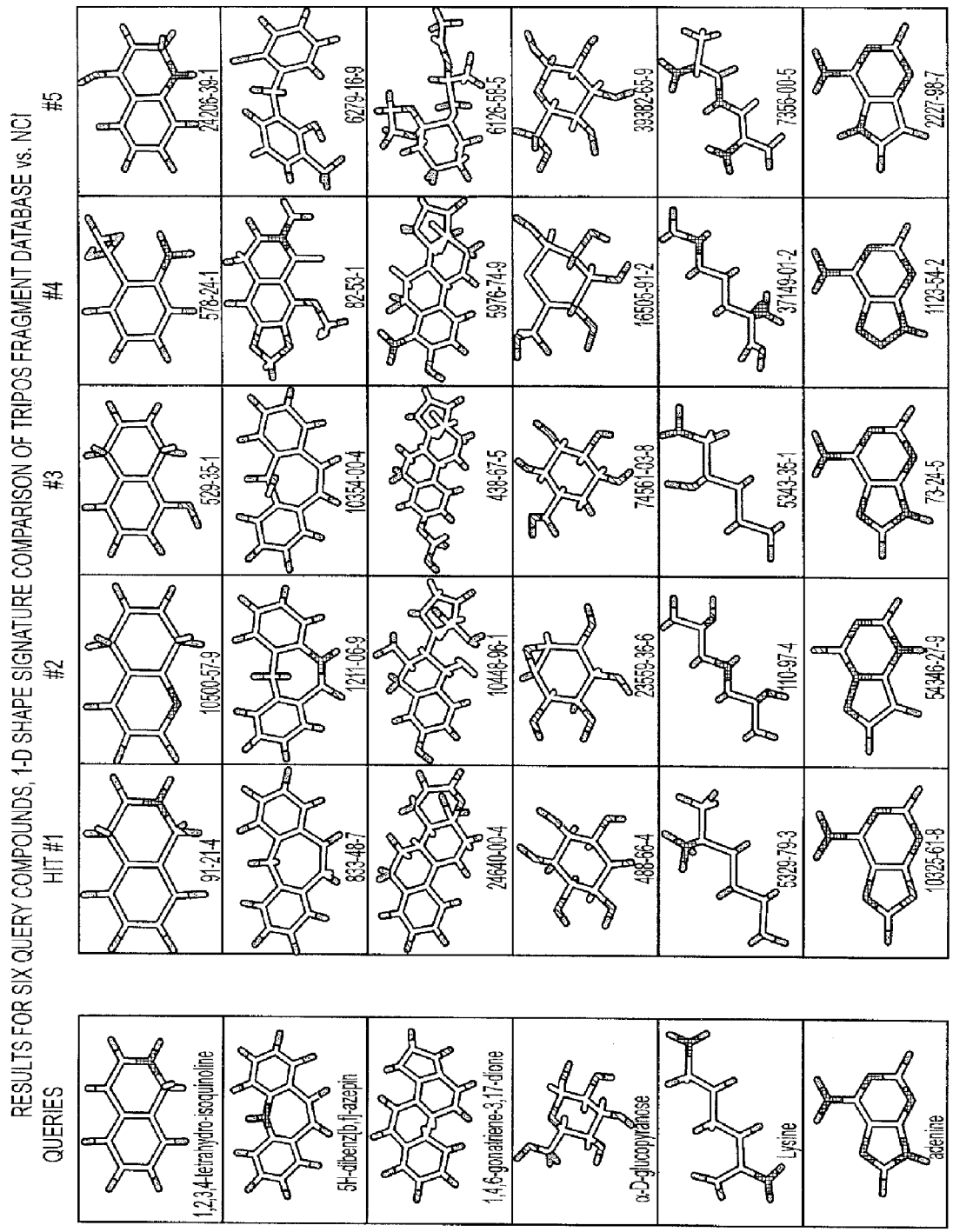

FIG. 16A lists top 1D hits for molecules from the Tripos fragment database used as queries against the NCI chemical library. The format of the table follows that of FIG. 14A, using the same queries and displaying results for 1D shape signatures, but in this table the score columns correspond to the use of different metrics $L_1$ and $R_1$, rather than having segment culling enabled or disabled. (Segment culling was used exclusively in preparation of the NCI shape signatures database, so there is no "non-culled" case to compare to.) The hits are labeled by NCI compound IDs (CAS). The top five hit structures for each query are displayed in FIG. 16B.

Of the six queries shown, only 1,2,3,4-tetradihydroisoquinoline and adenine are in the NCI database subset used in these searches. In the case of 1,2,3,4-tetradihydroisoquinoline, the NCI entry (CAS #91-21-4) corresponding to the query is selected as the top hit, while for adenine the corresponding hit (CAS #73-24-5) appears in the third position in the hit list. In the latter case, the top hit (CAS #10325-61-8) differs from adenine only in the substitution of an amine nitrogen with an oxygen, leading to structures that are very similar in shape; furthermore the scores of #73-24-5 and #10325-61-8 differ by only 0.004 probability units. Given the probabilistic nature of the method and the presence of competing structures of almost identical shape, the "best" chemical structure will not always top the hit list. Also, small differences in the conformation of query and target compounds may influence the order of hits.

The other queries locate target compounds that are generally of very similar structure. Some interesting and initially unexpected hits: for query 1,2,3,4-tetradihydroisoquinoline, the hit #578-54-1 is seen to have the same structure as the query, but with the amine-containing ring opened; for query 5H-dibenz[b,f]azepin, hit #6279-16-9 is similar to the query, but with the central ring opened. This ability to locate "approximate" matches is an interesting feature of the shape signatures approach. Hit #82-53-1 for query 5H-dibenz[b,f]azepin clearly bears a weak resemblance to the query despite a low score. This false positive is to be expected as the discussed method collapses a large space of chemical structures onto a comparatively small descriptor space. Hits under the $R_1$ metric are similar to those under $L_1$, involving for some queries the introduction of new hits, but more often simply the reordering in ranking of existing hits.

Figure 17B:
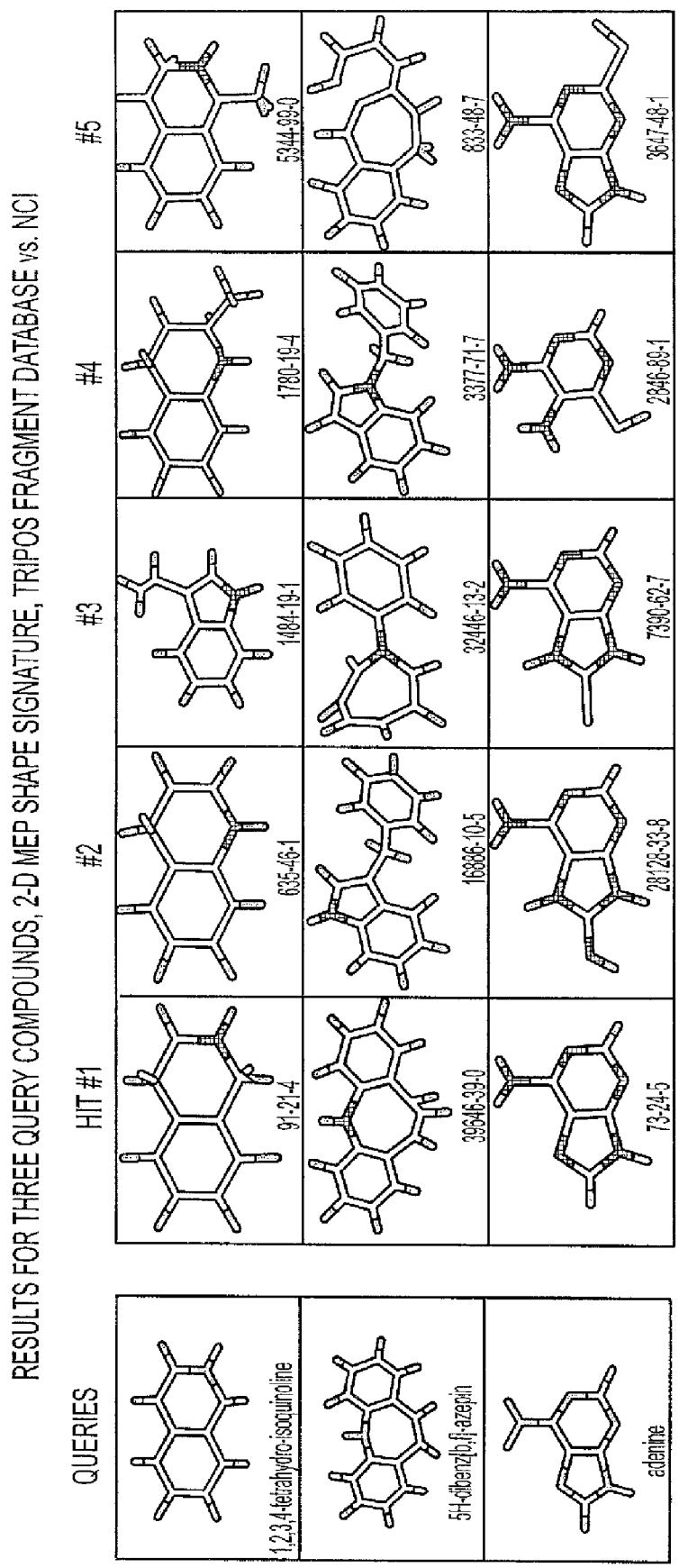

In FIG. 17A there is presented the results for the six query compounds when used in 2D shape signature searches against the NCI database. Despite the much larger size of the NCI database compared to the Tripos fragment database, only three of the queries (1,2,3,4-tetrahydroisoquinoline, 5H-dibenz[b,f]azepin and adenine) have clearly significant hits (with top scores less than 0.1) and one other (1,4,6-gonatriene-3,17-drone) has hits of borderline significance (with scores all larger than 0.15). Structures for the three low-scoring queries are shown in FIG. 17B.

Examination of these hits, and comparison to FIG. 16B, illustrates the role that electrostatics plays in selecting compounds. The hits for 1,2,3,4-tetradihydroisoquinoline all exhibit an electronegative nitrogen in a position identical or close to that found in the query. This is not the case for the 1D shape signature search where there is less consistency in the appearance of electronegative atoms in the hits. (In both the 1D and 2D searches, the query compound appears as the top hit.) For 5H-dibenz[b,f]azepin, the top 2D hit has somewhat weaker shape similarity compared to the top 1D hit, including a cyclopropyl motif not found in the query; at the same time it includes an electronegative nitrogen at a position homologous to that of the query. The top hit is followed by hits that arguably exhibit weaker shape similarity to the query than some of the corresponding 1D hits, but which include an electronegative nitrogen at a position similar to the query. Finally, hit #5 for the 2D-MEP search is the compound found as hit #1 in the 1D search. For adenine, the 2D-MEP search produces hits which in every case contain nitrogens at positions homologous to the query. Compound #2846-89-1 is an interesting "substructure match." The top hit in this case is the query, while in the 1D search the query molecule appeared as the #3 hit.

Searching the NCI shape signature database (113,331 compounds) using a 1D shape signature query required on average 133 sec on a 450 MHz PENTIUM™ III (a circuit chip) processor running the Linux operating system. This corresponds to 1.17 msec per comparison (which should be compared to the figure of 370 μsec quoted above for a 1.5 GHz machine). The average time per comparison for a 2D shape signature search was 3.7 msec.

For 1D searches, a distance of 0.05 or less in the metrics usually corresponded to strong shape similarity, while the range 0.05-0.1 is a borderline region where interesting hits may be mixed with "substructure" matches. For 2D-MEP searches under $L_1$ the corresponding ranges are 0-0.1 and 0.1-0.2. There should be a relatively small number of close hits for a given query. In contrast, the vast majority of target compounds should be unambiguously assigned as weak matches.

Figure 11A:
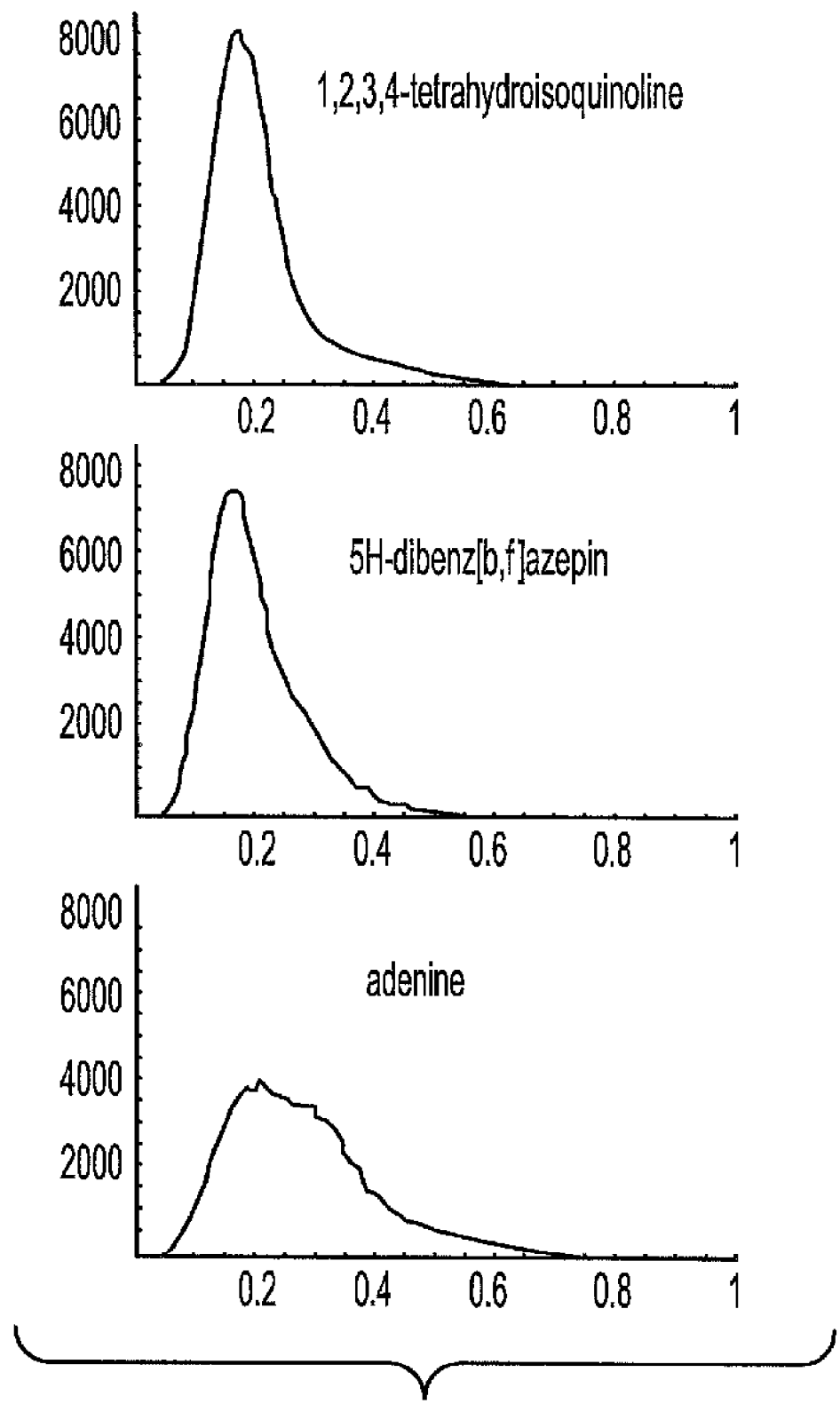
FIGS. 11A and 11B provide for score distributions for Example 3 using a linear axis.
Figure 11B:
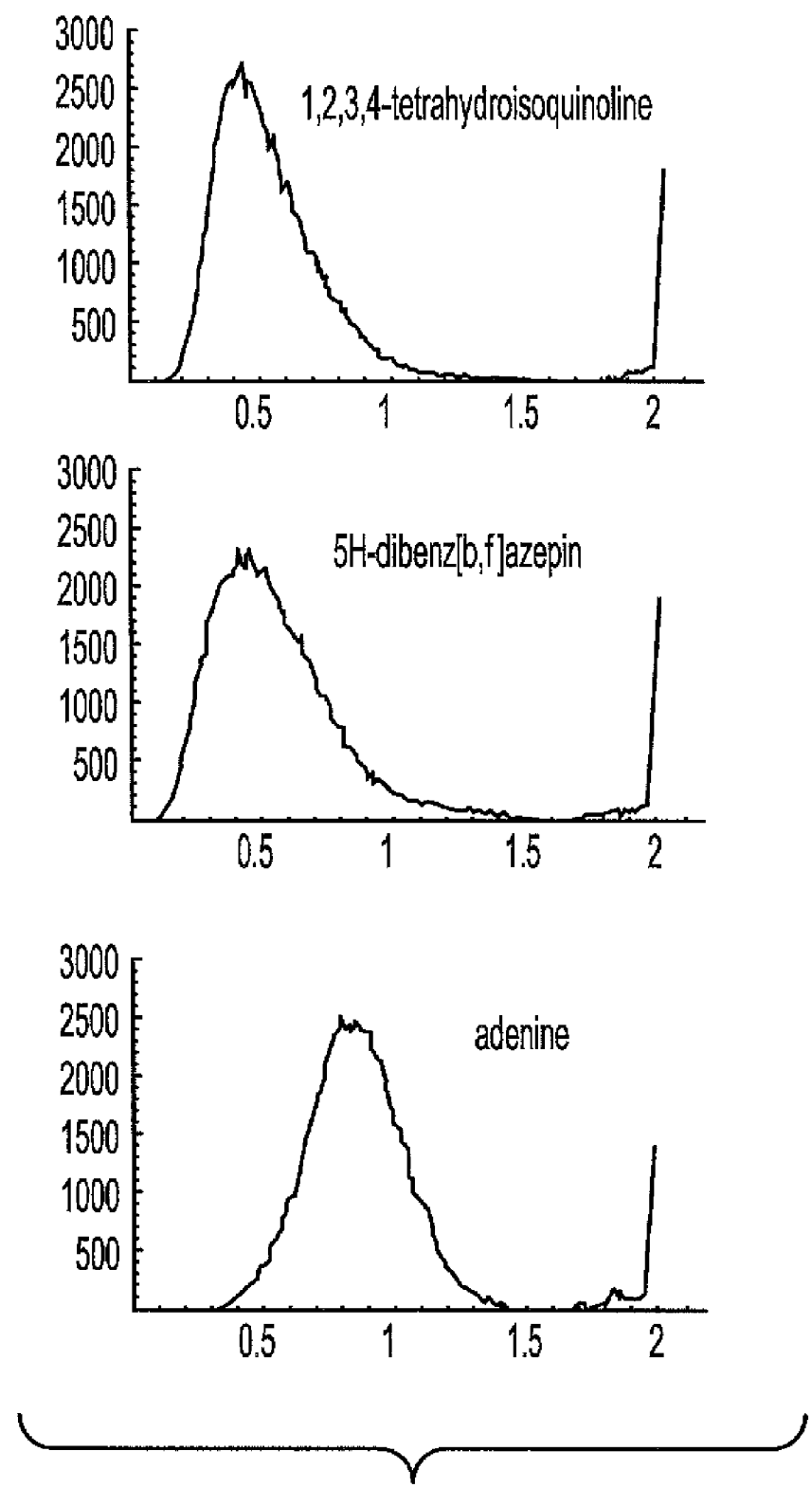

In FIG. 10A there is shown the distributions of 1D scores for the three query compounds of FIG. 17B. FIG. 10B shows the distributions of 2D scores for these molecules using the $L_1$ metric. These two FIGS. include a logarithmic axis for the number of compounds observed for a given range of scores. FIGS. 11A and 11B show the same distributions as FIGS. 10A and 10B but with linear vertical axes. FIG. 10 highlights the numbers of compounds observed at the extreme left of the distribution, where structurally-interesting matches are expected, while FIG. 11 provides a better sense of the shapes of the distributions, which appear to be locally Gaussian but with a significant shoulder. This gives the strong impression of being well-represented by a sum of two Gaussians, an observation that may be of practical significance for developing rapid tests for the significance of hits.

Given these distributions, the cutoff score needed to select a given percentage of-compounds in the NCI database can be directly computed. For a database of this size, two useful cutoffs are those needed to select 0.1% and 0.01% of the compounds, corresponding to approximately 100 and 10 compounds.

Noteworthy are the appearance of approximate and substructure matches as the scores increase. A general impression is that as scores increase, one observes first close matches, then hits that correspond to substructures or rearrangements of the query, and finally to hits that exhibit no clear similarity to the query. This allows identification of compounds that have at least partial similarity to an active compound, and which may be able to mimic a subset of the interactions of the query with a target receptor.

Example 4

The HIV protease inhibitor Indinavir was used as a starting framework. As shown in FIG. 1, the compound includes pyridine (101), t-butyl forinamide (103), phenyl (105), and benzocyclopentanol (107) as substituents, which are attached to a framework containing piperazine, a peptide group, and a central hydroxyl which marks the site of the transition state analogue presented by the inhibitor.

Rather than attempt to find receptor-based matches to the entire binding site, the embodiment of finding matches to receptor subsites was used. Those subsites were defined by excising these substituents one at a time from the experimental complex of the inhibitor and the native protease molecule. In this way four separate subsites were generated, each marked with a SYBYL™ (computer program for modeling) dummy atom attached to the portion of the inhibitor that remained. One of these sites, (101), was largely exposed to solvent and did not provide a well-defined, enclosed pocket; it was omitted from the analysis below, and the original substituent (pyridine) was retained at this position.

Ray-tracing was performed in each pocket with 50,000 reflections, and the ray traces were used to generate 1D shape signatures using ray-trace segment length for the three sites considered (103), (105) and (107). These were used to search the NCI database for compounds of shape similar to the pocket volumes (or stated another way, of shape complementary to the receptor subsites). Parameters were identical to those used in the ligand-based searches discussed in the prior examples.

Figure 12:
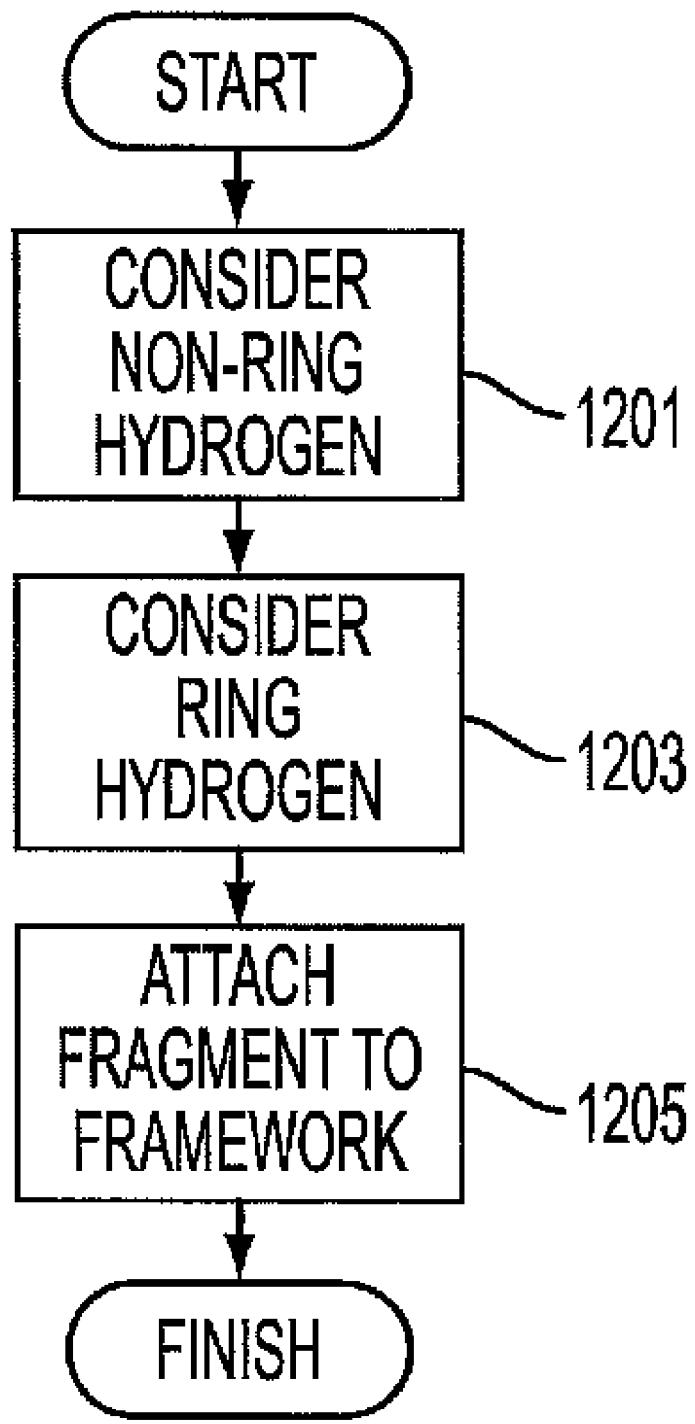
FIG. 12 provides a simplified flowchart of the steps performed by the ALMS computer program to attach hits to the framework.

Once a collection of hits was assembled for each subsite, the hits were attached to the framework. This was done using a custom SYBYL™ (computer program for modeling) application program called ALMS, for Automated Ligand-binding with Multiple Substitutions. The program was written in the SYBYL™ (computer program for modeling) programming language (SPL). A general flowchart of the program is shown in FIG. 12. In step (1201) each non-ring hydrogen of an NCI hit molecule was considered as a possible attachment point; in step (1203) each ring hydrogen as a possible attachment point through an added methylene carbon was considered. In this way, a single hit molecule was "exploded" into a family of fragments, each with a single free valence, marked by a dummy atom. In step (1205) a fragment is attached to the framework by removing the dummy atoms on both the hit and the target inhibitor site, and replacing these with a single bond linking the inhibitor and the fragment. The orientation of the newly-attached fragment was then optimized using Flexi-Dock, the genetic-algorithm-based optimizer included with the SYBYL™ (computer program for modeling) modeling package. Default force-field settings were used in FlexiDock (including hydrogens with reduced van der Waals radius and epsilon parameter), and in all calculations the genetic algorithm proceeded for 500 generations.

Each framework variable site was considered individually, with additions of all the fragments generated from the best n hits for a particular site carried out with the substituents of the starting inhibitor in place at all the other sites. The FlexiDock inhibitor-receptor interaction energies computed after adding all of the fragments targeted to a particular site were used to rank the fragments for that site. Next, the top k, m and n fragments for sites (103), (105), and (107) respectively were added in all possible combinations, with precomputed optimized geometry, generating k*m*n ligand molecules. A final energy minimization was performed in the field of the frozen receptor for each ligand, followed by an updated computation of the interaction energy. The interaction energies so computed were used to rank the table of putative inhibitors finally generated.

Figure 13A:
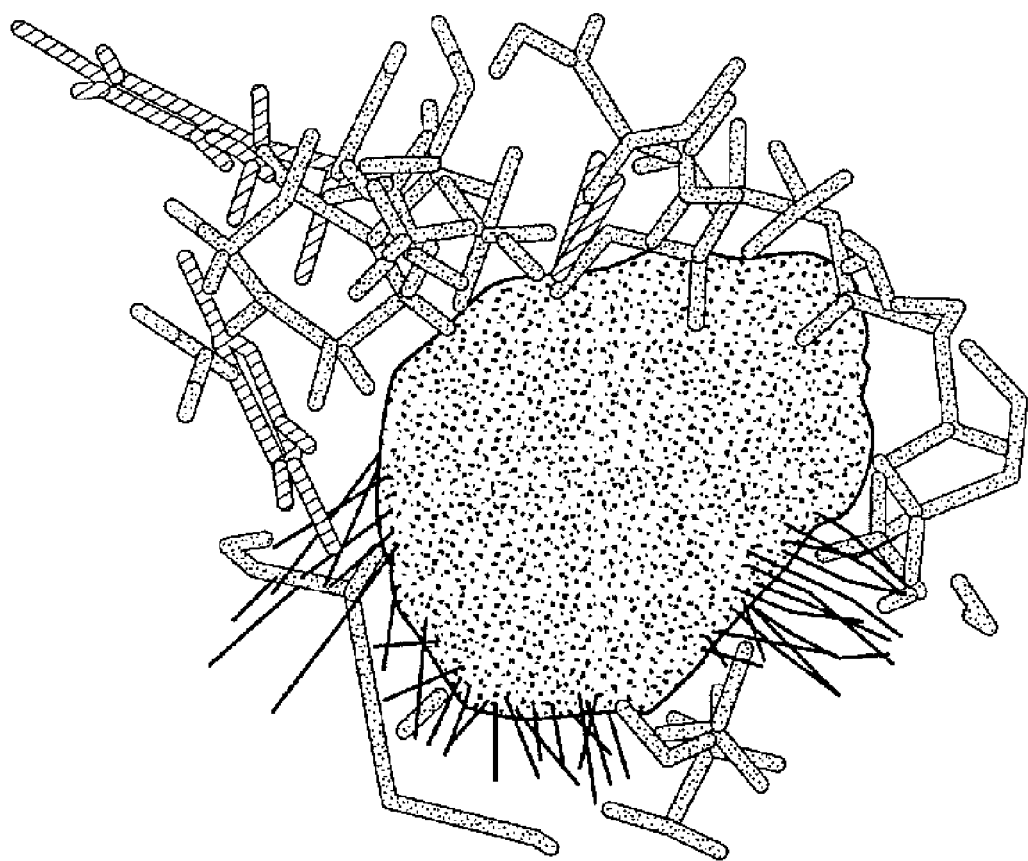
FIGS. 13A, 13B and 13C provide for an embodiment of ray-traces in HIV Protease subsites shown in FIG. 1. Protein atoms are involved in defining a site; framework atoms are distinguished by atom type. All subsite atoms appear in capped-stick rendering.
Figure 13B:
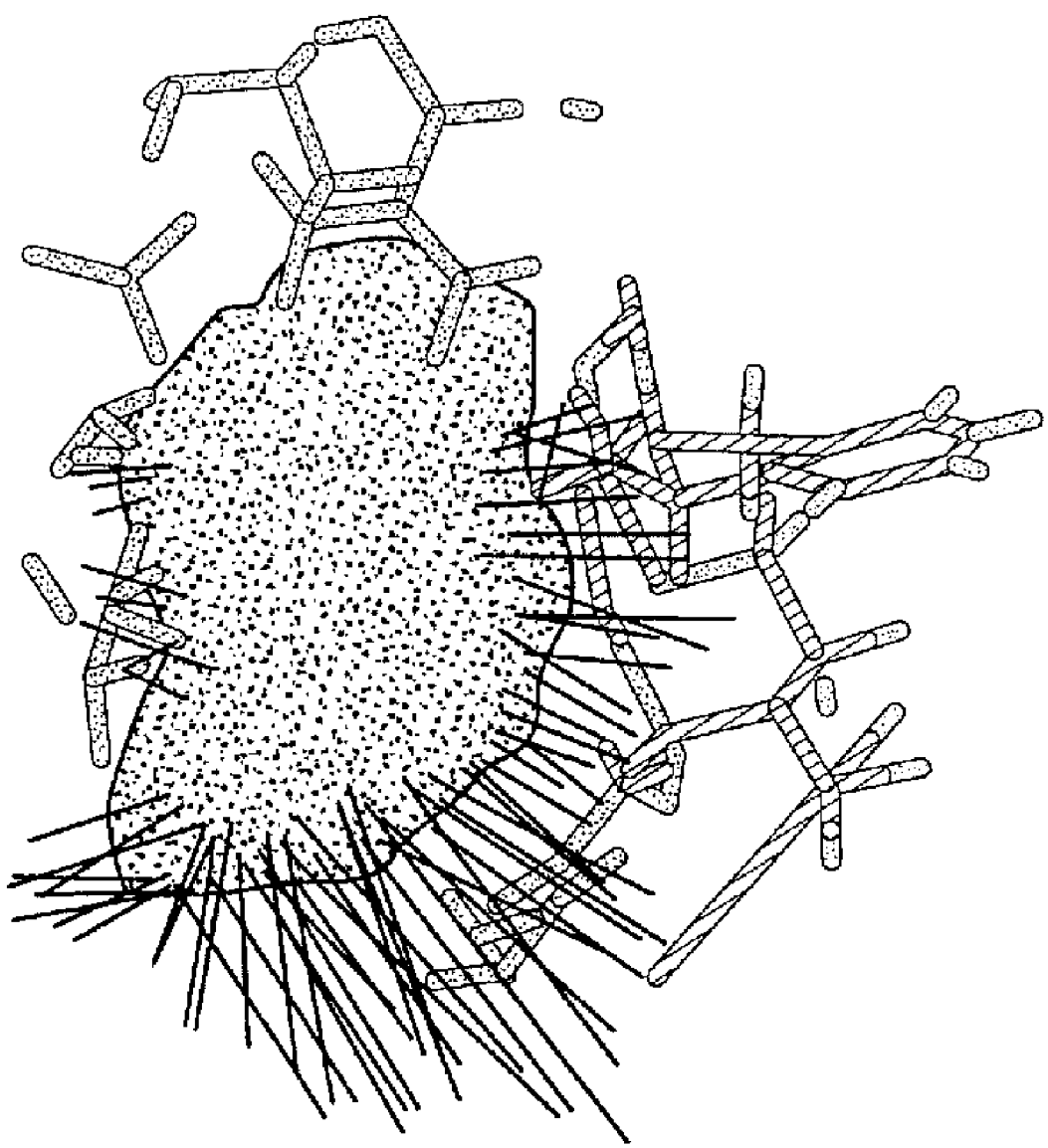
Figure 13C:
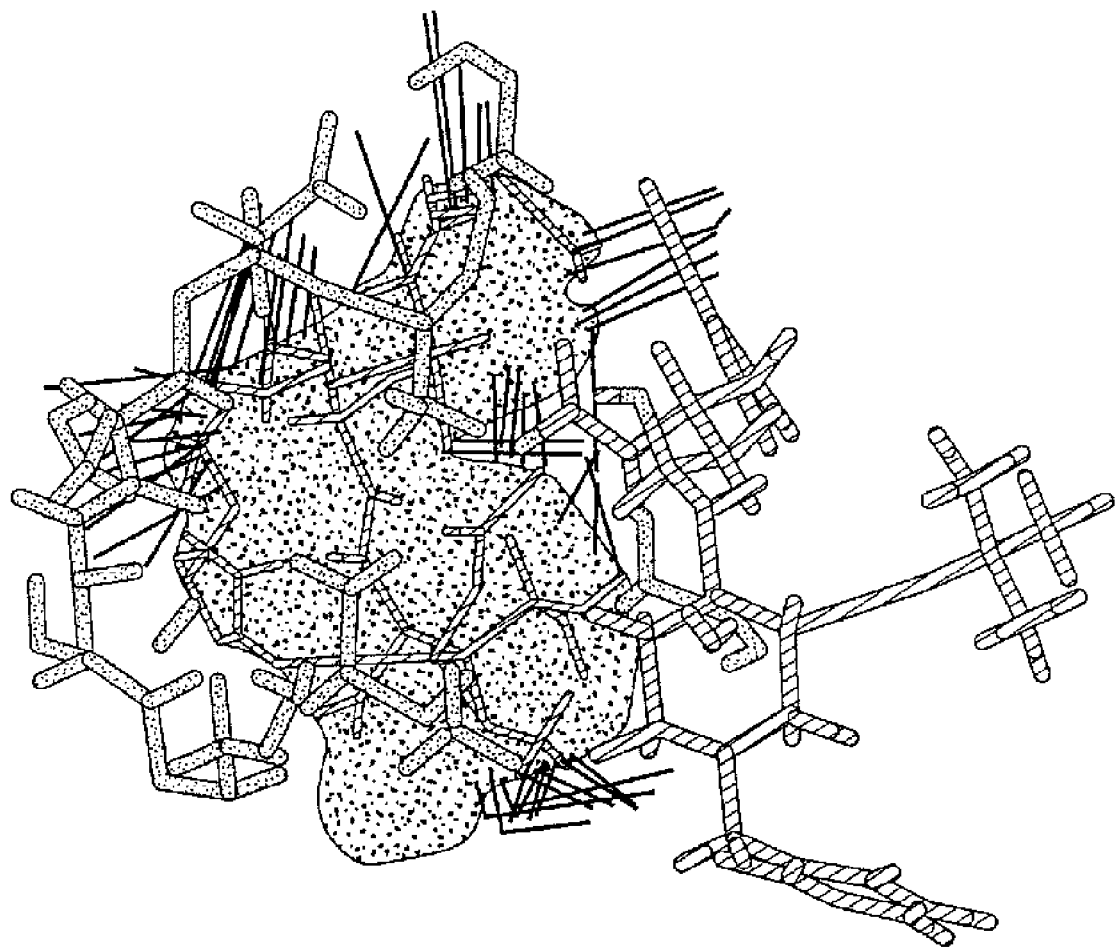

FIG. 13A shows the receptor subsite created by removing the (103) substituent (t-butyl formamide) from the Indinavir framework, along with the associated ray-trace. FIG. 13B shows the corresponding results for the (105) substituent, and FIG. 13C shows the ray-trace for the (107) substituent. Lines projecting from the receptor show rays that reflected out of the receptor subsite into infinity.

Figure 18:
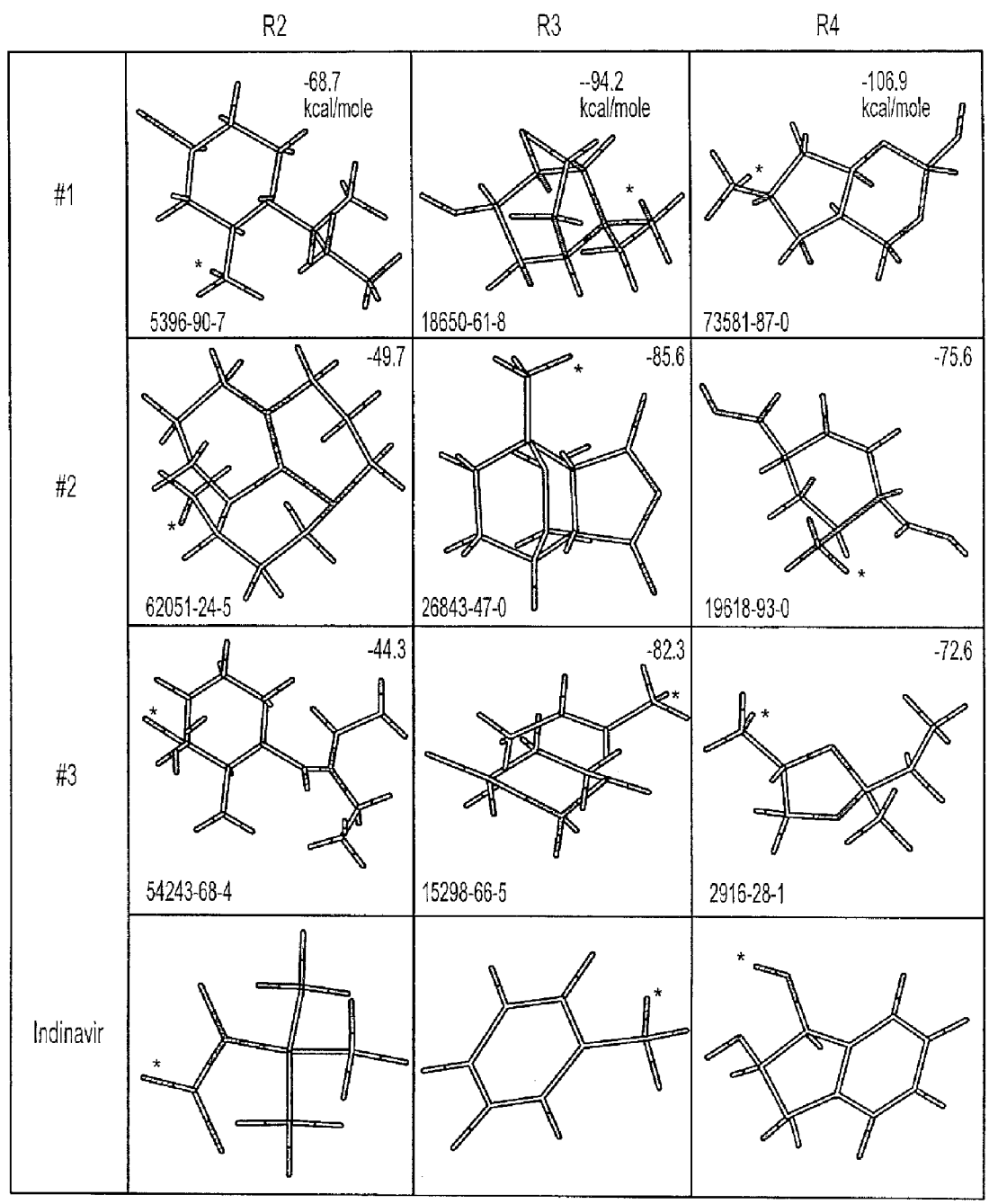
FIG. 18 provides an embodiment of the best NCI-derived fragments in molecular form for subsites $R_2$ (103), $R_3$ (105), and $R_4$ (107) as well as the CAS number of the source compound and the optimized energy. Indinavir is shown for comparison.

The top fifty hits for each of the subsite queries were examined, and it was found that in each hit set there were many examples of closely-related structures (this was especially the case with the list for substituent (107)). Subsets of structures with high similarity were identified in each list, and only one representative compound from each set was retained in an effort to assemble a structurally-diverse group of NCI hit compounds for each subsite. This yielded 27 compounds for substituent (103), 40 for substituent (105) and 12 for substituent (107). After exploding each hit by assignment of all possible attachment points, there were a total of 377 fragments for substituent (103) 275 for substituent (105), and 108 for substituent (107). Each fragment was attached to its target inhibitor site and optimized as described above. The selection of NCI hit compounds implied a total of 11,196,900 possible inhibitor structures. FIG. 18 shows the best three fragments for each subsite, ranked by FlexiDock energy realized after attachment and optimization, along with the CAS ID number for the source NCI compound. FIG. 18 also shows for comparison the substituent found at the same position in Indinavir.

To construct a collection of trial inhibitor structure, the best ten fragments for each of the three variable sites were selected, and inhibitors were constructed using all possible combinations of the selected fragments. Each selected fragment was attached to its target site with the FlexiDock-optimized conformation determined in the first phase of the procedure. This produced 1,000 initial structures. Interaction- and self-energies of all the compounds were computed by a utility in ALMS, which continued by ranking the compounds in order of ascending energy. The best fifty compounds were selected for energy minimization in the field of the frozen receptor.

The last phase of this "semi-automated" inhibitor design included generating a rough estimate of binding energy for each of the best fifty inhibitors. This involved removing the inhibitor (with optimized geometry) from the receptor and allowing it to minimize in isolation. Subtracting this minimized energy from the self-energy of the compound when docked provided an estimate of inhibitor strain energy, and this positive quantity was then added to the optimized inhibitor-receptor interaction energy to provide a binding energy estimate. Obviously this simple estimate did not take entropic factors into account, nor receptor flexibility.

All computations with SYBYL™ (computer program for modeling) were carried out on a Silicon Graphics workstation. Total computing time can be divided into that required for the following phases: Attachment of 760 fragments to their respective inhibitor sites, followed by optimization using FlexiDock, 5.45 hr; generation of 1,000 trial inhibitors, and initial computation of interaction energy, 1.49 hr; final minimization (1,000 steps max.) of best 50 inhibitors, 4.7 hr. Total CPU time was thus approximately 11.6 hr. The time required to scan the NCI database using the receptor-based shape signature queries was approximately 9 minutes (carried out on 550 MHz PENTIUM™ (computer chip) III processors running Linux).

Three representative inhibitors proposed by this procedure are shown in FIG. 19, along with their estimated binding energies. Indinavir is included for comparison (its binding energy estimate was derived from the crystal structure, using the same protocol described above). Most of the top-ranking inhibitors involve combinations of a small selection of substituents at the three variable sites; all of the best-scoring compounds had the same fragment (derived from compound #18650-61-8) at the substituent (107) position. Twenty-three of the inhibitors designed by our procedure have an estimated binding energy lower than −100 kcal/mole, and are predicted to be better binders than Indinavir.

While the invention has been disclosed in connection with certain preferred embodiments, this should not be taken as a limitation to all of the provided details. Modifications and variations of the described embodiments may be made without departing from the spirit and scope of the invention, and other embodiments should be understood to be encompassed in the present disclosure as would be understood by those of ordinary skill in the art.

The invention claimed is:

1. A computer-implemented method for determining molecular-shape of a receptor comprising:
    having a first molecule with a determined solvent-accessible molecular surface, wherein said surface includes a receptor which can be visualized within a computer;
    restricting said visualization of said surface to said receptor;
    said computer visualizing said molecular surface of said receptor as a plurality of small area elements;
    defining an initial start point in one of said plurality of small area elements and defining an initial direction;
    said computer having available instructions for defining a ray segment, said instructions comprising:
        starting an in-process ray at a start point;
        propagating said in-process ray in a direction until said in-process ray impacts another of said small area elements at an impact point, resulting in a ray segment between said start point and said impact point;
        recording characteristics of said ray segment including electrostatic properties of said impact point and said start point, said impact point, and said start point;
    said computer processor performing a ray-trace by repeatedly performing said instructions for defining ray segments until a plurality of ray segments is obtained wherein:
        in said first performance of said instructions, said start point of said in-process ray comprises said initial start point and said direction of said in-process ray comprises said initial direction; and
        in each subsequent performance of said instructions, said start point of said in-process ray comprises said impact point from the immediately prior ray segment and said direction of said in-process ray comprises the direction of reflection of said immediately prior ray segment from said impact point;
    said computer processor stopping said instructions for said in-process ray when a predetermined stop condition is met;
    if stopped:
        said computer processor restarting said instructions for said in-process ray at the same start point, and propagating said in-process ray in a direction which does not comprise the direction of reflection of said immediately prior ray segment from said impact point; and
    finishing said ray trace once a preselected number of ray segments have been recorded;
    said computer corresponding said ray segments to atoms;
    said computer partitioning said molecule into atom clusters;
    said computer decomposing said ray trace by assigning said ray segments according to results of said step of corresponding, wherein each said ray segment is assigned at least in fractional part to at least one segment corresponding to an atom cluster (an intra-cluster segment) or atoms between atom clusters (an inter-cluster segment);
    said computer calculating a unique probability distribution for each said intra-cluster segment and each said inter-cluster segment based on characteristics of said assigned ray segments, said probability distribution providing an indication of the shape of said inter-cluster segment or said inter-cluster segment; and
    said computer storing said probability distribution for later comparison to other probability distributions indicative of shapes of other molecules or portions thereof, wherein said other probability distributions are in a database.

2. The method of claim 1 further comprising:
    said computer generating a target volume, said target volume functionally corresponding to said receptor;
    wherein said generating utilizes physical surface tension.

3. The method of claim 1 further comprising:
    said computer scaling said ray segments.

* * * * *